(12) United States Patent
Frankowski et al.

(10) Patent No.: US 8,734,382 B2
(45) Date of Patent: May 27, 2014

(54) INTRACORPOREAL GAS EXCHANGE DEVICES, SYSTEMS AND METHODS

(75) Inventors: Brian J. Frankowski, Imperial, PA (US); William J. Federspiel, Pittsburgh, PA (US); Kevin M. Mihelc, Somerville, MA (US); Samuel C. Lieber, Jersey City, NJ (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 556 days.

(21) Appl. No.: 12/865,958

(22) PCT Filed: Feb. 6, 2009

(86) PCT No.: PCT/US2009/033399
§ 371 (c)(1),
(2), (4) Date: Aug. 3, 2010

(87) PCT Pub. No.: WO2009/100336
PCT Pub. Date: Aug. 13, 2009

(65) Prior Publication Data
US 2010/0331767 A1    Dec. 30, 2010

Related U.S. Application Data

(60) Provisional application No. 61/026,735, filed on Feb. 7, 2008.

(51) Int. Cl.
*A61M 37/00* (2006.01)
*A61M 1/00* (2006.01)
(52) U.S. Cl.
USPC .................................. 604/26; 604/23; 604/27
(58) Field of Classification Search
USPC ......... 128/DIG. 3; 604/23, 24, 25, 26, 27, 43, 604/45, 93.01, 264, 523, 524, 525
See application file for complete search history.

(56) References Cited

U.S. PATENT DOCUMENTS

| | | | |
|---|---|---|---|
| 4,135,253 | A | 1/1979 | Reich |
| 4,406,656 | A | 9/1983 | Hattler |

(Continued)

FOREIGN PATENT DOCUMENTS

| | | |
|---|---|---|
| WO | WO2007146162 A2 | 12/2007 |
| WO | WO2009100336 | 8/2009 |

OTHER PUBLICATIONS

Paul, R et al. Shear Stress Related Blood Damage in Laminar Couette Flow, Artif Organs, 2003, 27, 517-529.

(Continued)

*Primary Examiner* — Kevin C Sirmons
*Assistant Examiner* — Shefali Patel
(74) *Attorney, Agent, or Firm* — Bartony & Associates, LLC

(57) ABSTRACT

A system for intracorporeal gas exchange includes a flexible, rotatable shaft; a plurality of axially spaced agitation mechanisms positioned on the rotatable shaft, such that the rotatable shaft can flex between the axially spaced agitation mechanisms; a plurality of hollow gas permeable fibers adapted to permit diffusion of a gas between an intracorporeal fluid and an interior of the hollow fibers. The plurality of hollow fibers is positioned radially outward from the agitation mechanisms. A blood contacting medical system includes at least one seal, and a purge system via which a flushing fluid is introduced under pressure over a blood-side face of the at least one seal and caused to flow through a space on the blood-side face of the at least one seal. The system can further include a rotatable member. The space on the blood-side face of the at least one seal can be in fluid connection with an annular space adjacent to a rotating element operatively connected to the rotatable member.

17 Claims, 29 Drawing Sheets

(56) References Cited

U.S. PATENT DOCUMENTS

| | | | |
|---|---|---|---|
| 4,625,712 A * | 12/1986 | Wampler | 600/16 |
| 4,846,791 A | 7/1989 | Hattler | |
| 4,911,689 A | 3/1990 | Hattler | |
| 4,986,809 A | 1/1991 | Hattler | |
| 5,122,113 A | 6/1992 | Hattler | |
| 5,207,640 A | 5/1993 | Hattler | |
| 5,219,326 A | 6/1993 | Hattler | |
| 5,271,743 A | 12/1993 | Hattler | |
| 5,376,069 A | 12/1994 | Hattler | |
| 5,501,663 A * | 3/1996 | Hattler et al. | 604/26 |
| 5,865,789 A | 2/1999 | Hattler | |
| 6,673,594 B1 * | 1/2004 | Owen et al. | 435/284.1 |
| 7,763,097 B2 | 7/2010 | Federspiel | |
| 2002/0198560 A1 | 12/2002 | Boyle | |
| 2003/0133835 A1 * | 7/2003 | Hattler | 422/45 |
| 2006/0063142 A1 | 3/2006 | Owen | |
| 2006/0264810 A1 * | 11/2006 | Hattler et al. | 604/26 |

OTHER PUBLICATIONS

Budilarto, Stephanus G. et al. Flow Visualization Study of a Pulsating Respiratory Assist Catheter, ASAIO Journal, 2005, 673-680.
Eash, Heide J. et al. Acute In Vivo Testing of a Respiratory Assist Catheter: Implants in Calves Versus Sheep, ASAIO Journal, 2003, 370-377.
Eash, Heide J. et al. Evaluation of Fiber Bundle Rotation for Enhancing Gas Exchange in a Respiratory Assist Catheter, ASAIO Journal, 2007, 368-373.
Eash, Heide J. et al. Evaluation of Local Gas Exchange in a Pulsating Respiratory Support Catheter, ASAIO Journal, 2005, 152-157.
Eash, Heide J. et al. Evaluation of Plasma Resistant Hollow Fiber Membranes for Artificial Lungs, ASAIO Journal, 2004, 491-497.
Eash, Heide J. et al. Investigating the Effects of Random Balloon Pulsation on Gas Exchange in a Respiratory Assist Catheter, ASAIO Journal, 2006, 192-195.
Federspiel, William J. et al. Lung, Artificial: Basic Principles and Current Applications, Encyclopedia of Biomaterials and Biomedical Engineering, 2004, 910-921.
Federspiel, William J. et al. Lung, Artificial: Current Research and Future Directions, Encyclopedia of Biomaterials and Biomedical Engineering, 2004, 922-931.
Federspiel, William J. et al. Experimental Evaluation of a Model for Oxygen Exchange in a Pulsating Intravascular Artificial Lung, Annals of Biomedical Eng, 2000, 28, 160-167.
Federspiel, William J. et al. Ex Vivo Testing of the Intravenous Membrane Oxygenator, ASAIO Journal, 2000, 261-267.
Federspiel, William J. et al. Gas Flow Dynamics in Hollow-Fiber Membranes, AIChE Journal, 1996, 42, 7, 2094-2099.
Federspiel, William J. et al. Recent Progress in Engineering the Pittsburgh Intravenous Membrane Oxygenator ASAIO Journal, 1996, 42, M435-442.
Federspiel, William J. et al. Sweep Gas Flowrate and CO2 Exchange in Artificial Lungs, Artificial Organs, 1996, 20, 9, 1050-1052.
Garcia, Monica Y. et al. Effect of Vessel Compliance on the In-Vitro Performance of a Pulsating Respiratory Support Catheter, Journal of Biomechanical Engineering, 2002, 124, 56-62.
Golob, Joseph F. et al Acute In Vivo Testing of an Intravascular Respiratory Support Catheter, ASAIO Journal, 2001, 432-437.
Hattler, Brack G et al. A Respiratory Gas Exchange Catheter: In Vitro and in Vivo Tests in Large Animals, Journal of Thoracic and Cardiovascular Surgery, 2002, 520-530.
Hattler, http://alung.com/hattlerCatheter.html, Hattler Catheter, ALung Technologies, published Oct. 10, 2007.
Hattler, Brack G et al. Gas Exchange in the Venous System: Support for the Failing Lung, The Artificial Lung, 2002, Chapter 6, 134-174.
Hattler, Brack G et al. Progress with the development of the Intravenous Membrane Oxygenator, Perfusion, 1999, 14, 311-315.
Hattler, Brack G et al. The artificial Lung, The Cambridge University Press, 2003, 386-398.
Hewitt, Todd J. et al. A Mathematical Model of Gas Exchange in an Intravenous Membrane Oxygenator, Annals of Biomedical Engineering, 26, 1998, 166-178.
Hout, Marian S. et al. Validation of a Model for Flow-Dependent Carbon Dioxide Exchange in Artificial Lungs, Artif. Organs, 2000, 24, 2, 114-118.
Lund, Laura W. et al. A Comparative In Vitro Hemolysis Study of a Pulsating Intravenous Artificial Lung, ASAIO Journal, 2002, 631-635.
Lund, Laura W. et al. Gas Permeability of Hollow Fiber Membranes in a Gas-Liquid System, Journal of Membrane Science, 1996, 117, 207-219.
Lund, Laura W. et al. Gas Permeance Measurement of Hollow Fiber Membranes in Gas-Liquid Environment, AIChE Journal, 2002, 48, 3, 635-643.
Lund, Laura W. et al. Is Condensation the Cause of Plasma Leakage in Microporous Hollow Fiber Membrane Oxygenators, Journal of Membrane Science, 1998, 147, 87-93.
Nolan, Timothy D. C. et al. Development of a Balloon Volume Sensor for Pulsating Balloon Catheters, ASAIO Journal, 2004, 225-233.
Snyder, Trevor A. et al. Blood Biocompatibility Assessment of an Intravenous Gas Exchange Device, Artif. Organs, 2006, 30, 9, 657-664.
Konishi, Ruriko et al. Nitric Oxide Prevents Human Platelet Adhesion to Fiber Membranes in Whole Blood, ASAIO J., 1996, 42(5), M850-M853.
Macha, Mahender et al. Acute In Vivo Studies of the Pittsburgh Intravenous Membrane Oxygenator, ASAIO J., 1996, 42(5), M609-M615.
Lund, Laura W. et al. A Novel method for Measuring Hollow Fiber Membrane Permeability in a Gas Liquid System, ASAIO J., 1996, 42(5), M446-M451.
Federspiel, Willian et al., Development of a Low Resistance Intravenous Oxygenator, ASAIO J., 1997, 43(5), M725-M730.

* cited by examiner

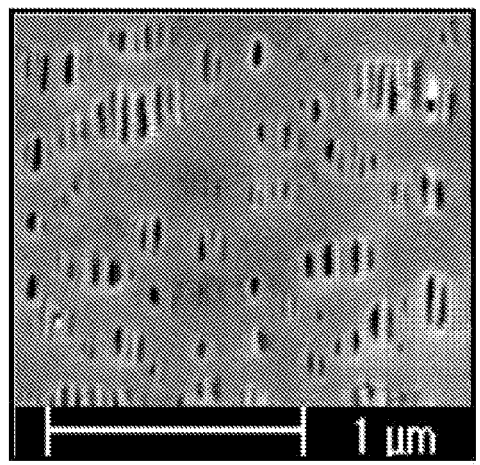
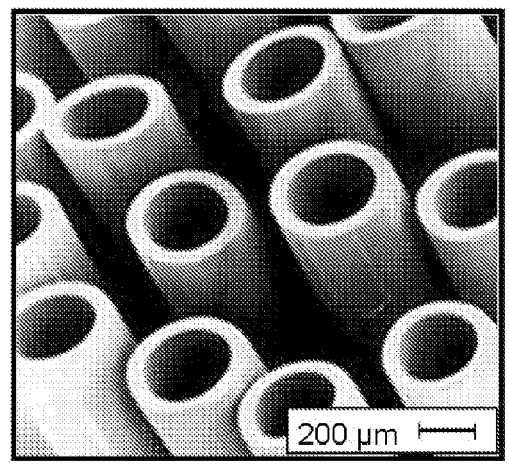
Fig. 2A — Microporous fiber wall
Fig. 2B — Bundle cross-section
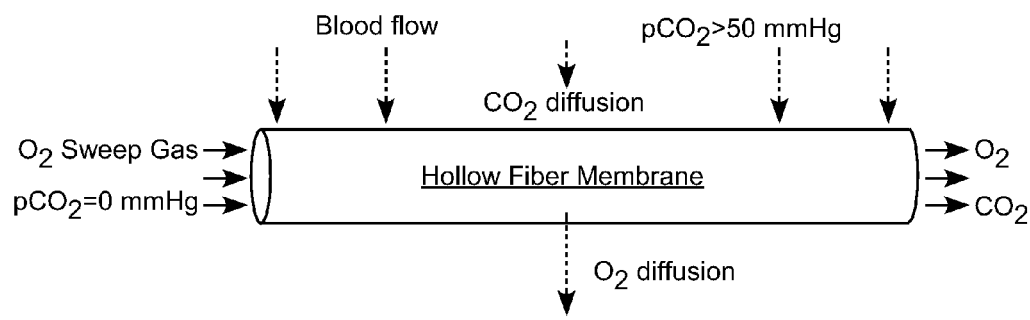
Fig. 3

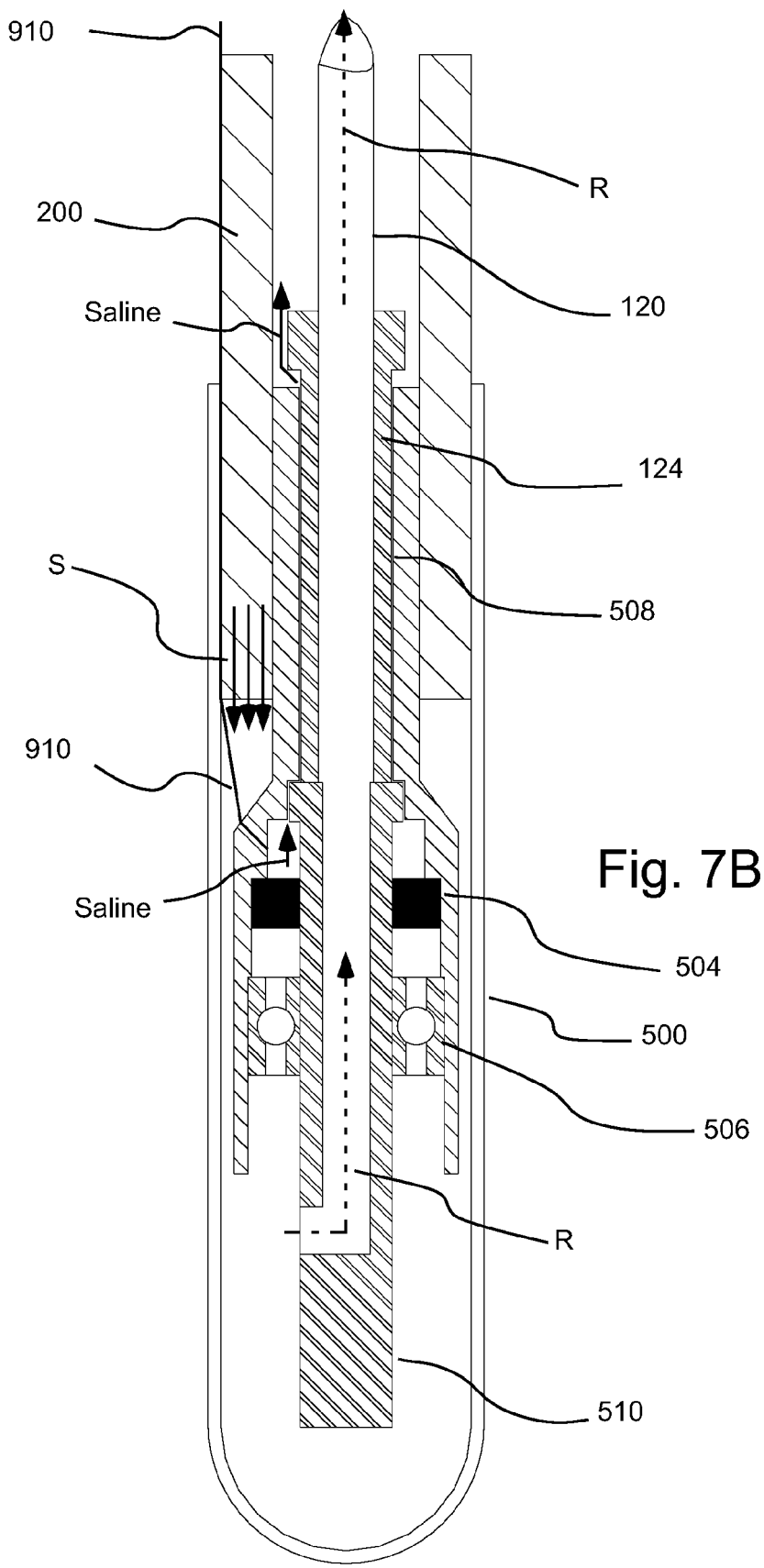

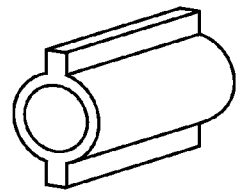
Fig. 8A (1)
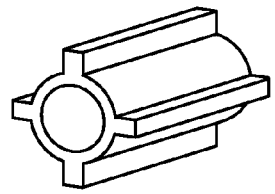
Fig. 8A (2)
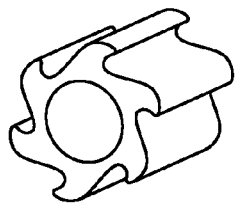
Fig. 8A (3)
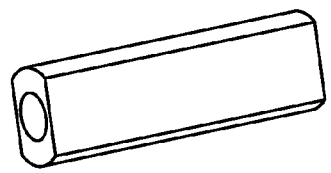
Fig. 8A (4)
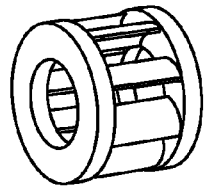
Fig. 8A (5)
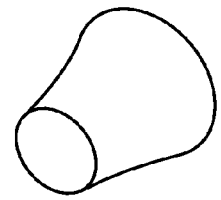
Fig. 8A (6)
Fig. 8A (7)
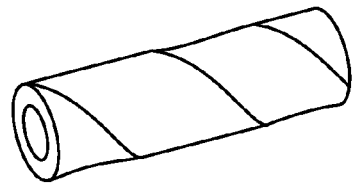
Fig. 8A (8)

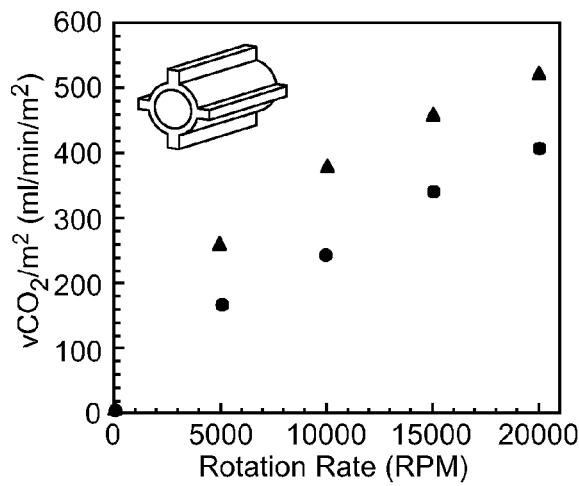
Fig. 9E (1)
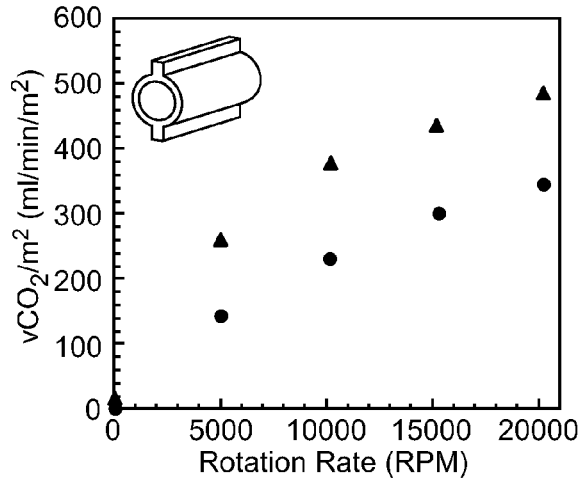
Fig. 9E (2)
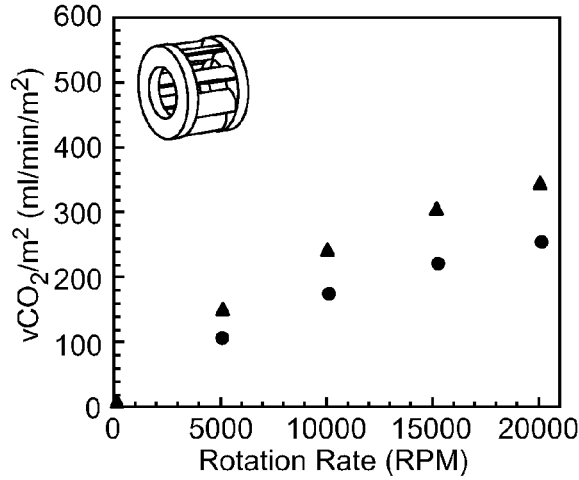
Fig. 9E (3)

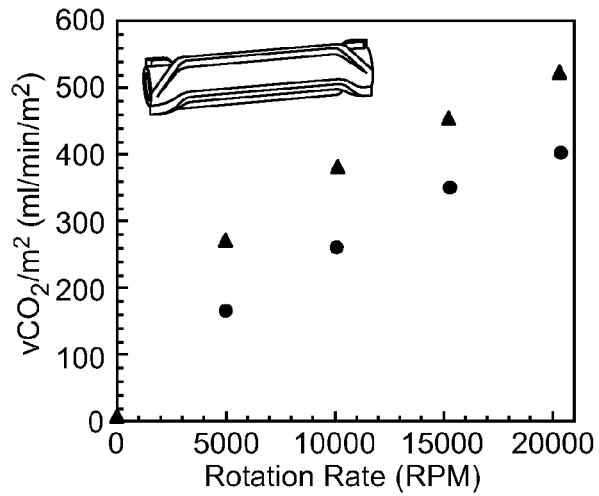
Fig. 9E (4)
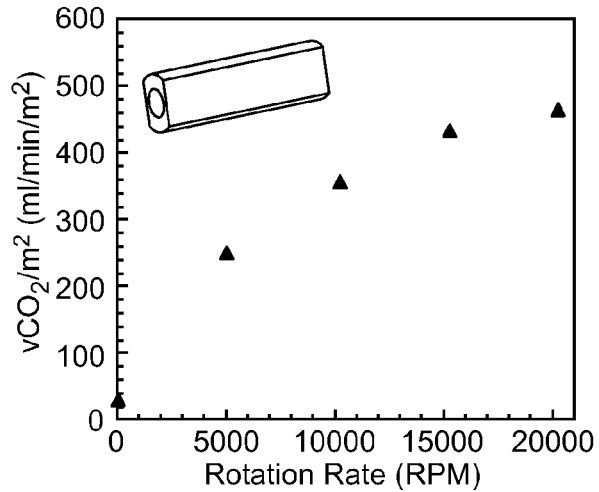
Fig. 9E (5)
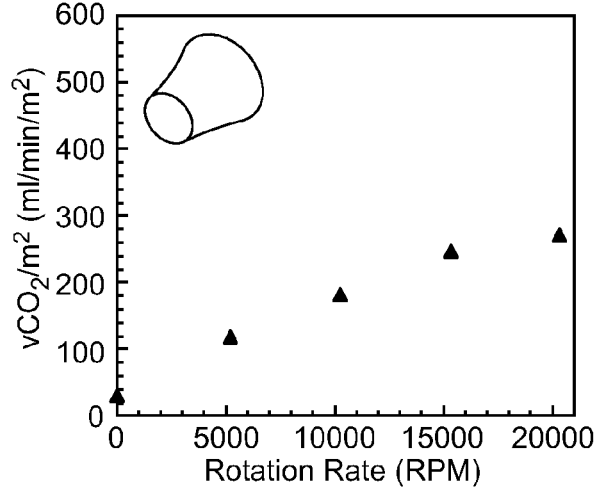
Fig. 9E (6)

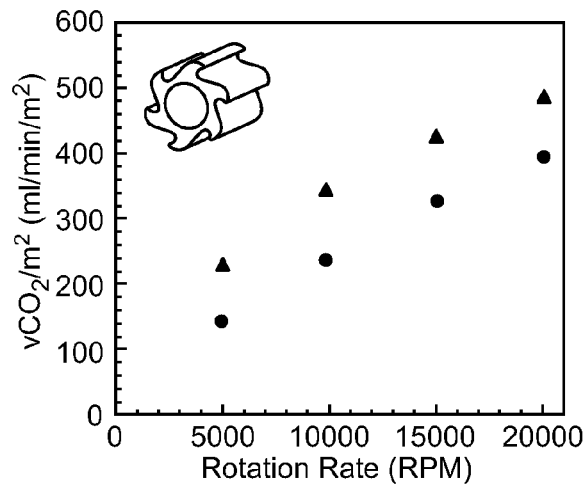
Fig. 9E (7)
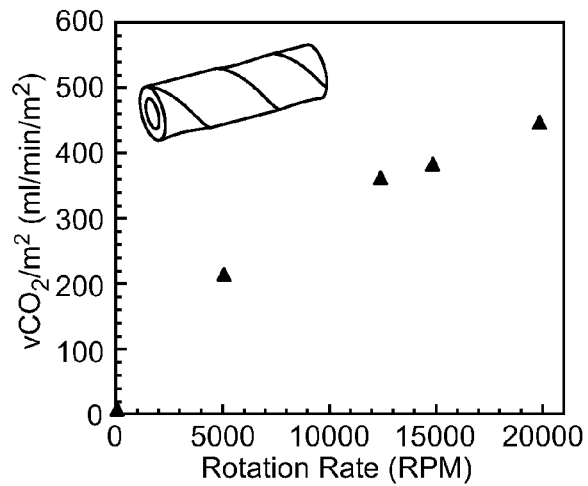
Fig. 9E (8)
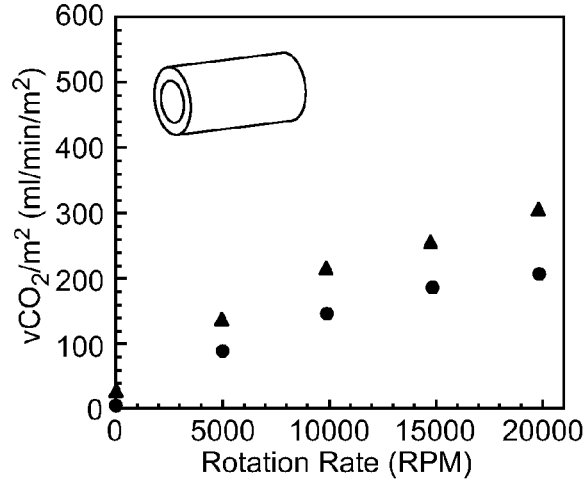
Fig. 9E (9)

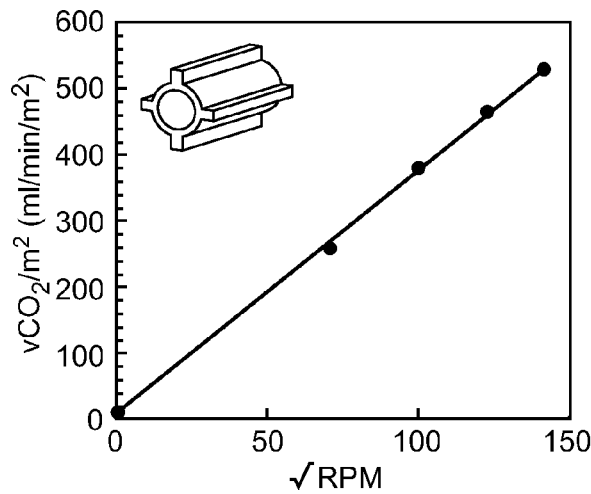
Fig. 9F (1)
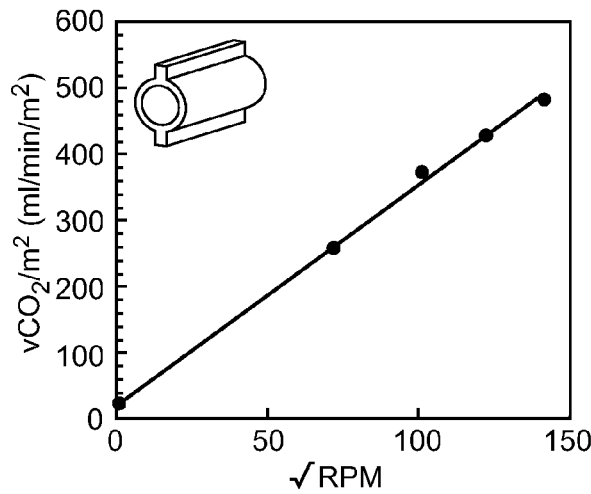
Fig. 9F (2)
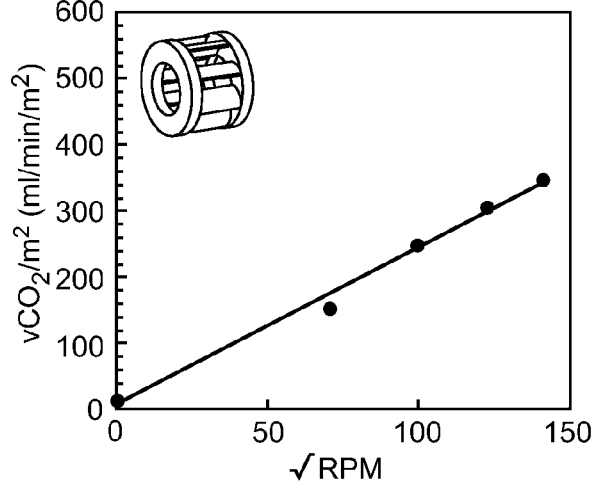
Fig. 9F (3)

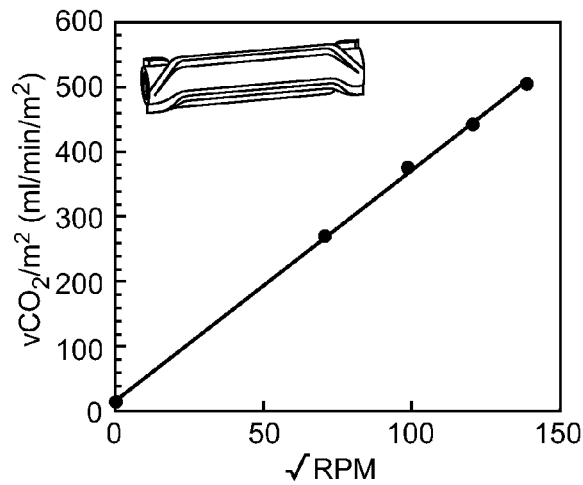
Fig. 9F (4)
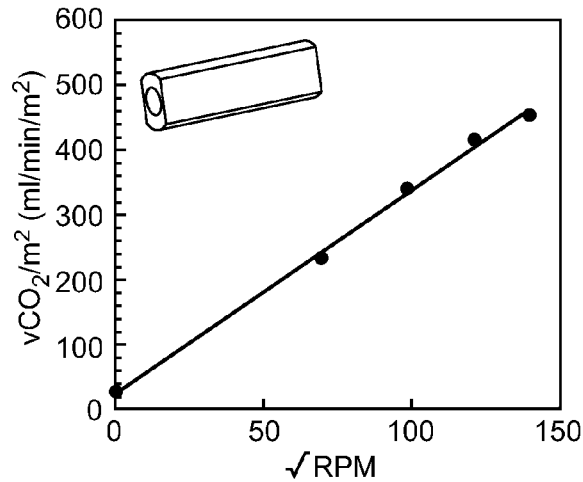
Fig. 9F (5)
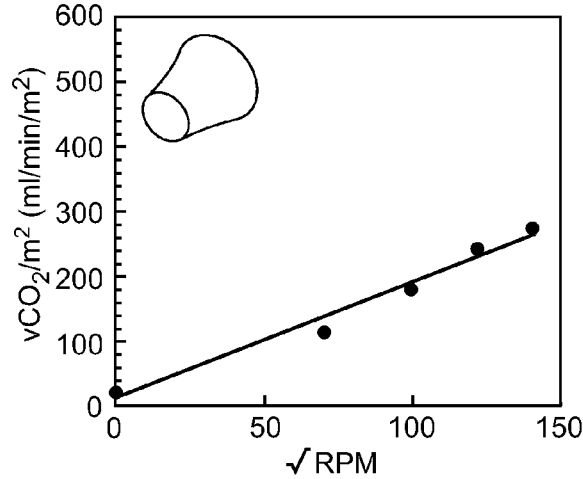
Fig. 9F (6)

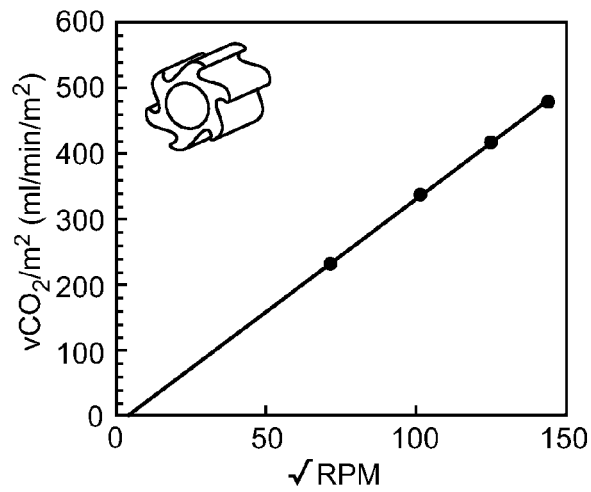
Fig. 9F (7)
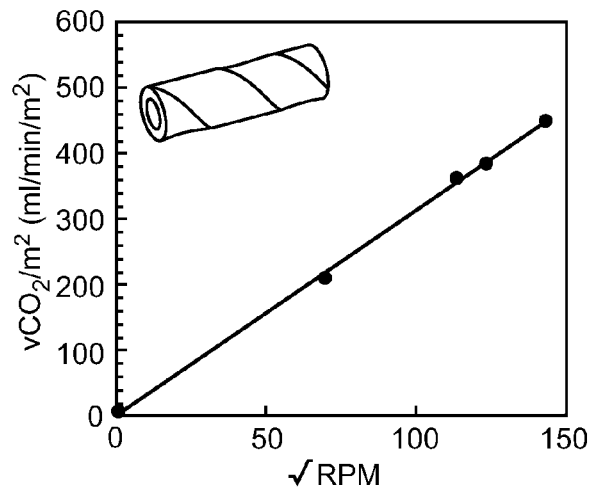
Fig. 9F (8)
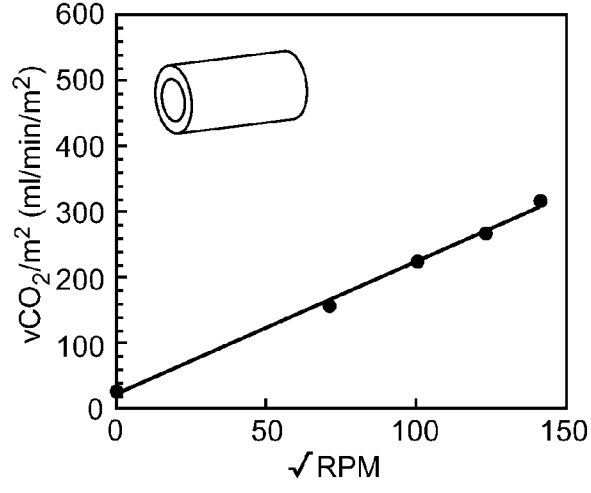
Fig. 9F (9)

A: 1.50" bending radius
B: 0.630" inner diameter

INTRACORPOREAL GAS EXCHANGE DEVICES, SYSTEMS AND METHODS

CROSS-REFERENCE TO RELATED APPLICATION

The present application is a 371 of PCT/US2009/033399, filed on Feb. 6, 2009 which claims benefit of U.S. Provisional Patent Application Ser. No. 61/026,735, filed Feb. 7, 2008, the disclosures of which are incorporated herein by reference.

GOVERNMENTAL INTEREST

This invention was made with government support under grant HL070051awarded by the National Institute of Health: National Heart, Lung and Blood Institute. The government has certain rights in this invention.

BACKGROUND OF THE INVENTION

The present invention relates to intracorporeal gas exchange devices, systems and methods and, particularly, to devices, systems and method to effect gas exchange within a patient's vascular structure.

The following information is provided to assist the reader to understand the invention disclosed below and the environment in which it will typically be used. The terms used herein are not intended to be limited to any particular narrow interpretation unless clearly stated otherwise in this document. References set forth herein may facilitate understanding of the present invention or the background of the present invention. The disclosure of all references cited herein are incorporated by reference.

Lung disease remains one of the major healthcare problems present in the United States today. Two significant contributors to lung disease are acute respiratory distress syndrome (ARDS), and chronic obstructive pulmonary disease (COPD).

Acute respiratory distress syndrome is defined as a severe syndrome of inflammation and increased vascular permeability that is associated with a constellation of clinical, radiologic, and physiologic abnormalities. It is a non-cardiogenic, acute respiratory complication characterized by a profound reduction in systemic oxygenation or ventilation, with an in-hospital mortality rate of 38.5%. ARDS develops as a result of injury to the endothelium and epithelial layers of the alveolar membrane from stimuli such as sepsis, infection or trauma. The breakdown of the capillary-alveolar barrier leads to alveolar flooding and an eventual deterioration of gas exchange capability.

In contrast to ARDS, chronic obstructive pulmonary disease is a persistent, irreversible condition that slowly progresses over time. COPD refers to the existence or coexistence of chronic bronchitis and emphysema and is characterized by obstructed airways, enlarged air spaces and destruction of lung parenchyma, occlusion of small airways, and reduced lung elasticity. When compared to normal, healthy lung function, patients with advanced stages of COPD can experience 10 to 20 times the work necessary to facilitate breathing.

Hospital treatment for ARDS, acute exacerbations of COPD, and advanced COPD exist in three broad generalizations: pharmacological, mechanical ventilation and application of an extracorporeal membrane device (artificial lung). The treatment modalities depend on the severity of the disease as well as patient response to prior therapies. As indicated by the high mortality rates for the lung conditions, however, each therapy has associated limitations which can interrupt patient discharge from the hospital and/or recovery.

The least invasive and first line of defense in treating lung failure is to administer drugs that may improve the ailing condition. Multiple pharmacologic strategies have been investigated since the 1960's, but despite therapeutic benefits, none of the investigated treatments have demonstrated an ability to improve patient survival.

Mechanical ventilation is the most common therapy and serves to maintain respiratory function by rhythmically inducing a controlled flow of air into the lungs. In healthy persons, normal breathing consists of contracting the diaphragm to distend the lungs and create a negative pressure from atmosphere to lungs forcing fresh air in. Following oxygen and carbon dioxide gas exchange, the diaphragm relaxes compressing the lungs and forcing expiratory air to the external environment. Mechanical ventilation creates this effect but in an opposing manner; fresh air is driven into the lungs by positive pressure and expiratory air is pumped out of the lungs by a negative pressure.

Mechanical ventilation treatment is associated with multiple shortcomings termed ventilator-induced lung injury, or VILI. VILI covers a range of detrimental insults to the lung that can postpone recovery, cause unfavorable outcomes, or even intensify preexisting injury.

The third clinical therapy being administered utilizes a membrane oxygenator and accompanying flow circuit. The treatment is denoted as extracorporeal membrane life support (ECLS), often times referred to as extracorporeal membrane oxygenation (ECMO). An ECLS device processes patient blood by adding oxygen and removing carbon dioxide through fiber membrane technology, replicating the natural gas exchange function of the lungs.

ECLS is employed under circumstances of severe, reversible respiratory failure or to patients responding adversely to all advanced modes of mechanical ventilation. Operation of the circuit relies on a pump to draw blood from the vena cava, transport it through the membrane oxygenator, and return the blood either to the right atrium (venovenous bypass) or aorta (venoarterial bypass). Patients still receive mechanical ventilation while on ECLS, however settings are reduced to minimize VILI as a result of the ability of the oxygenator to exchange blood gases. With less required work from the lungs, ECLS permits physiological complications to abate and the therapy can be applied for weeks barring complications.

Limitations of ECLS primarily arise from external circuitry and artificial blood contacting surfaces. To avert thrombosis within the circuit, patient blood is continuously anticoagulated and bleeding is a major risk whether internal (intercranial) or from cannula dislodgement. Patients are paralyzed and/or heavily sedated to minimize movement causing dislodgement, which creates a high risk scenario for decubitis ulcers. Also, the continuous exposure of the blood to artificial surfaces causes platelets to adhere and/or alter function (thrombocytopenia) requiring the patient to receive multiple platelet transfusions. In addition, the ECLS circuit must be constantly monitored for mechanical failures such as tubing degradation, oxygenator or pump failure, and presence of gaseous emboli or clot formation. Other noted complications include sepsis and renal failure. Finally, ECLS requires a multidisciplinary team to provide care. Staffing and overall cost of the procedure, as well as restriction to major medical centers are further limitations to providing this therapy.

Recently, there have been attempts to develop intracorporeal artificial lung devices. Percutaneous, intravascular respiratory support therapy, which refers to treatments employing a gas exchange device or an artificial lung device within the vasculature of a patient to supplement lung function, can be used as an additional and/or alternative approach to treating ARDS and acute exacerbations of COPD. Such devices typically use hollow fiber membrane or HFM technology to achieve gas exchange, oxygenating blood and removing carbon dioxide. In most situations, carbon dioxide removal is a primary goal of intravascular devices since sufficient oxygenation levels can be attained in the clinical setting through nasal oxygen or specific ventilation modes.

The ability of intravascular respiratory support devices to facilitate carbon dioxide removal from the circulation provides an advantage over sole mechanical ventilation strategies. By regulating hypercapnia (or elevated carbon dioxide levels in the blood), intravascular respiratory therapy can allow ventilation at lower tidal volumes and pressures and thereby eliminate the deleterious effects that often develop with mechanical ventilation. Decrease in mechanical ventilation intensity to support patients has been demonstrated to improve mortality rates. In addition, the diseased lung tissue experiences a lower workload since the device itself is performing partial respiratory function. The reduced workload allows the injured tissue to rest and may improve tissue recovery.

ECLS is able to regulate hypercapnia but is associated with a number of complications resulting from blood circulating outside the body. Utilizing an intracorporeal/intravascular device eliminates external circuitry, thereby lessening the risks of thrombocytopenia and activation of complement resulting from artificial surfaces. Less artificial surface can also result in lower anticoagulation levels thereby decreasing bleeding risks. Overall implementation of the intravascular respiratory therapy is easier than ECLS making it less demanding on hospital resources, less expensive, and potentially available in more hospitals.

Factors regulating gas exchange in the intravascular devices include gas partial pressures in both blood and fiber lumens, total HFM surface area, fiber bundle geometry and relative velocity at which the blood passes by the fiber surfaces. A concentration boundary layer that forms near the external walls of the individual fibers can result in significant resistance to diffusion that limits gas exchange. The boundary layer forms as a result of blood flow patterns around the fiber walls.

Existing intravascular devices can be categorized as either passive or active by the means in which boundary layer reduction is approached. Passive devices rely on blood flowrates and fiber bundle geometry to mix flow patterns and disrupt layer formation near stationary fibers. Active devices implement motion to the fiber membranes and or to the blood subjacent to the fiber membranes to disrupt boundary layer formation. In general, to increase gas exchange, additional surface area can be provided to boost overall diffusion and/or boundary layers can be reduced to decrease mass transfer resistance. High relative blood velocity to fibers facilitates boundary layer reduction.

As clear to those skilled in the art, a relatively small size is beneficial for intracorporeal/intravascular respiratory assist devices. Such devices can, for example, be inserted into a patient's vascular structure in the manner of a catheter. Reducing insertion size of the device is desirable to prevent tissue damage and facilitate placement. However, limiting the size of the intravascular device also results in limitations upon surface area of the gas exchange membrane system, thereby limiting gas exchange. Further, the amount of motion that can be imparted to blood and/or fibers to increase gas exchange efficiency is limited by potential damage to surrounding tissue and to the blood. Previously studied intracorporeal/intravascular devices have met with only limited success as a result of these limitations.

It thus remains desirable to develop improved intracorporeal gas exchange devices, systems and methods that are safe, effective, and/or amenable to easy insertion.

SUMMARY OF THE INVENTION

In one aspect, the present invention provides a system for intracorporeal gas exchange including a flexible, rotatable shaft; a plurality of axially spaced agitation mechanisms positioned on the rotatable shaft, such that the rotatable shaft can flex (more readily) between the axially spaced agitation mechanisms; a plurality of hollow gas permeable fibers adapted to permit diffusion of gas between intracorporeal fluid and an interior of the hollow fibers. The plurality of hollow fibers is positioned radially outward from the agitation mechanisms.

The system can further include a support member positioned radially outward from the agitation mechanisms. The plurality of hollow fibers can, for example, be positioned radially outward of and adjacent to the support member.

Each of the plurality of agitation mechanisms can, for example, include at least one radially outward extending vane.

The system can further include a medial manifold and a distal manifold. A first end of each of the plurality of hollow fibers can, for example, be in fluid connection with the medial manifold. A second end of each of the plurality of hollow fibers can be in fluid connection with the distal manifold. The device can further include a first fluid path for flow of an inlet gas into the medial manifold to flow into the first ends of the hollow fibers and a second fluid path in fluid connection with the distal manifold into which outlet gas exiting the second ends of the hollow fibers can flow to exit the device.

The system can also include an extracorporeal proximal manifold including an inlet in fluid connection with the first fluid path and an outlet in fluid connection with the second fluid path.

At least a portion of the second fluid path can be within the flexible rotatable shaft.

The system can also include a drive shaft and a drive system to impart rotation to the drive shaft. The drive shaft can, for example, pass through the proximal manifold and through the second fluid path to be in operative connection with the rotating shaft.

The system can further include a vacuum in fluid connection with the outlet of the proximal manifold.

In several embodiments, at least one of the medial manifold and the distal manifold includes at least one seal, and the device further includes a purge system via which a flushing fluid is introduced under pressure over a blood-side face of the seal and caused to flow through a space on the blood side of the seal. The space on the blood side of the seal can, for example, be in fluid connection with an annular space adjacent to a rotating element in operative connection with the rotatable shaft.

The medial manifold can, for example, include at least a first seal, and the distal manifold can include at least a second seal. The purge system can introduce flushing fluid under pressure over a blood-side face of the first seal and cause flushing to flow through a space on the blood side of the first seal. The purge system can also introduce flushing fluid under pressure over a blood-side face of the second seal and cause flushing fluid to flow through a space on the blood side of the second seal.

The space on the blood side of the first seal can be in fluid connection with an annular space adjacent to a first rotating element operatively connected to the rotatable shaft, and the space on the blood side of the second seal is an annular space adjacent to a second rotating element operatively connected to the rotatable shaft.

The purge system can further include a first conduit to deliver flushing fluid to the medial manifold and a second conduit to delivery flushing fluid to the distal manifold.

In several embodiments, the drive system and drive shaft are adapted to rotate the rotating shaft at a rate of at least 10,000 to 20,000 RPM.

The distal manifold, the hollow fibers and the medial manifold can, for example, be adapted to be inserted intravascularly and can have a maximum outer diameter of no more than 33 French or no more than 25 French.

In several embodiments, the device comprises immobilized carbonic anhydrase on or in the vicinity of at least a portion of a first surface of the hollow fibers.

The system can further include immobilized carbonic anhydrase on or in the vicinity of at least a portion of a first surface of the hollow fibers such that the immobilized carbonic anhydrase comes into contact with the fluid. The first surface can, for example, exhibit carbonic anhydrase activity of at least 20% of maximum theoretical activity of the first surface of the hollow fibers based on monolayer surface coverage of carbonic anhydrase in the case that the carbonic anhydrase is immobilized on the first surface of the hollow fibers.

In another aspect, the present invention provides a system for intracorporeal gas exchange including: a rotatable shaft; at least one agitation mechanism positioned on the rotatable shaft; a plurality of hollow gas permeable fibers adapted to permit diffusion of gas between intracorporeal fluid and an interior of the hollow fibers, the plurality of hollow fibers being positioned radially outward from the agitation mechanism; at least one seal, and a purge system via which a flushing fluid is introduced under pressure over a blood-side face of the seal and caused to flow through a space on the blood side of the seal. The space on the blood side of the seal can, for example, be in fluid connection with an annular space adjacent to a first rotating element operatively connected to the rotatable shaft.

In a further aspect, the present invention provides a blood contacting medical system including at least one seal, and a purge system via which a flushing fluid is introduced under pressure over a blood-side face of the seal and caused to flow through a space on the blood side of the seal. The system can further include a rotatable member. In several embodiments, the space on the blood side of the seal is in fluid connection with an annular space adjacent to a rotating element operatively connected to the rotatable member.

The devices of the present invention provide significant advantages over previously studied intracorporeal/intravascular gas exchange devices. To be effective and obtain clinical acceptance, such devices are preferably safe in operation, effective, and amenable to easy insertion. In general, these criteria require an intravascular device to be relatively small in size. In general, increased gas exchange efficiencies (both $CO_2$ removal and $O_2$ exchange) of the devices and systems of the present invention, allow the devices and systems to be fabricated with relatively small outer diameters. The devices of the present invention can, for example, be used for respiratory support of patients with acute or chronic lung failure. In many situations, the devices will be used for short periods of time (for example, two weeks or less) in clinical setting. In most cases, a primary performance goal will be $CO_2$ removal as sufficient oxygenation levels can usually be attained in a clinical setting through nasal oxygen or specific lung protective ventilation modes. The devices of the present invention can, for example, achieve $CO_2$ removal rates of at least 30 ml/min, at least 50 ml/min, and even at least 75 ml/min under normocapnia conditions. The devices of the present invention can facilitate ventilatory lung protective strategies by regulating hypercapnia conditions. Removal rates can increase under permissive hypercapnia.

The present invention, along with the attributes and attendant advantages thereof, will best be appreciated and understood in view of the following detailed description taken in conjunction with the accompanying drawings.

BRIEF DESCRIPTION OF THE DRAWINGS

FIG. 2A illustrates a photomicrograph of a fiber wall of a hollow fiber membrane.

FIG. 2B illustrates a perspective view of fiber ends of a hollow fiber membrane bundle.

FIG. 3 illustrates a model of gas exchange (oxygenation of and carbon dioxide removal from) blood via a hollow fiber membrane.

FIG. 7B illustrates an enlarged cross-sectional view of the distal manifold.

FIG. 8A(1) illustrates a "2-flat" impeller unit geometry studied in the present invention.

FIG. 8A(2) illustrates a "4-flat" impeller unit geometry studied in the present invention.

FIG. 8A(3) illustrates a "sawtooth" impeller unit geometry studied in the present invention.

FIG. 8A(4) illustrates a "paddle" impeller unit geometry studied in the present invention.

FIG. 8A(5) illustrates a "centrifugal" impeller unit geometry studied in the present invention.

FIG. 8A(6) illustrates a "cone" impeller unit geometry studied in the present invention.

FIG. 8A(7) illustrates a "RAX" impeller unit geometry studied in the present invention.

FIG. 8A(8) illustrates an "axial" impeller unit geometry studied in the present invention.

FIG. 9E(1) illustrates a graph of experimental results for carbon dioxide removal as a function of impeller rotation speed in deionized water and in a viscous fluid for the indicated impeller unit geometry.

FIG. 9E(2) illustrates a graph of experimental results for carbon dioxide removal as a function of impeller rotation speed in deionized water and in a viscous fluid for the indicated impeller unit geometry.

FIG. 9E(3) illustrates a graph of experimental results for carbon dioxide removal as a function of impeller rotation speed in deionized water and in a viscous fluid for the indicated impeller unit geometry.

FIG. 9E(4) illustrates a graph of experimental results for carbon dioxide removal as a function of impeller rotation speed in deionized water and in a viscous fluid for the indicated impeller unit geometry.

FIG. 9E(5) illustrates a graph of experimental results for carbon dioxide removal as a function of impeller rotation speed in deionized water and in a viscous fluid for the indicated impeller unit geometry.

FIG. 9E(6) illustrates a graph of experimental results for carbon dioxide removal as a function of impeller rotation speed in deionized water and in a viscous fluid for the indicated impeller unit geometry.

FIG. 9E(7) illustrates a graph of experimental results for carbon dioxide removal as a function of impeller rotation speed in deionized water and in a viscous fluid for the indicated impeller unit geometry.

FIG. 9E(8) illustrates a graph of experimental results for carbon dioxide removal as a function of impeller rotation speed in deionized water and in a viscous fluid for the indicated impeller unit geometry.

FIG. 9E(9) illustrates a graph of experimental results for carbon dioxide removal as a function of impeller rotation speed in deionized water and in a viscous fluid for the indicated impeller unit geometry.

FIG. 9F(1) illustrates a graph of experimental results for carbon dioxide removal as a function of the square root of impeller rotation speed for the indicated impeller unit geometry.

FIG. 9F(2) illustrates a graph of experimental results for carbon dioxide removal as a function of the square root of impeller rotation speed for the indicated impeller unit geometry.

FIG. 9F(3) illustrates a graph of experimental results for carbon dioxide removal as a function of the square root of impeller rotation speed for the indicated impeller unit geometry.

FIG. 9F(4) illustrates a graph of experimental results for carbon dioxide removal as a function of the square root of impeller rotation speed for the indicated impeller unit geometry.

FIG. 9F(5) illustrates a graph of experimental results for carbon dioxide removal as a function of the square root of impeller rotation speed for the indicated impeller unit geometry.

FIG. 9F(6) illustrates a graph of experimental results for carbon dioxide removal as a function of the square root of impeller rotation speed for the indicated impeller unit geometry.

FIG. 9F(7) illustrates a graph of experimental results for carbon dioxide removal as a function of the square root of impeller rotation speed for the indicated impeller unit geometry.

FIG. 9F(8) illustrates a graph of experimental results for carbon dioxide removal as a function of the square root of impeller rotation speed for the indicated impeller unit geometry.

FIG. 9F(9) illustrates a graph of experimental results for carbon dioxide removal as a function of the square root of impeller rotation speed for the indicated impeller unit geometry.

DETAILED DESCRIPTION OF THE INVENTION

In several embodiments, the present invention provides intracorporeal respiratory assist devices that can, for example, be inserted in a percutaneous manner similar to insertion of a catheter which are operable to at least partially support native lung function in patients with, for example, acute respiratory distress syndrome and/or acute exacerbations of chronic obstructive pulmonary disease. Intravascular devices of the present invention are sometimes referred to herein as catheters. As described above, primary current clinical therapies (including pharmacotherapy, mechanical ventilation, and ECLS) are associated with patient injury and high mortality rates. The devices of the present invention can be used in combination with or as an alternative to such clinical therapies to reduce patient injury and mortality.

Although the devices, systems and methods of the present invention are discussed primarily herein in connection with oxygenation of and removal of carbon dioxide from blood, one skilled in the art appreciates that the devices, systems and methods of the present invention can be used for many other types of gas exchange (for example, for delivery of anesthesia).

As used herein and in the appended claims, the singular forms "a," "an", and "the" include plural references unless the content clearly dictates otherwise. Thus, for example, (unless clearly indicated otherwise) reference to "an impeller unit" includes a plurality of impeller units and equivalents thereof known to those skilled in the art, and so forth, and reference to "the impeller unit", is a reference to one or more such impeller units and equivalents thereof known to those skilled in the art, and so forth.

Figure 1:
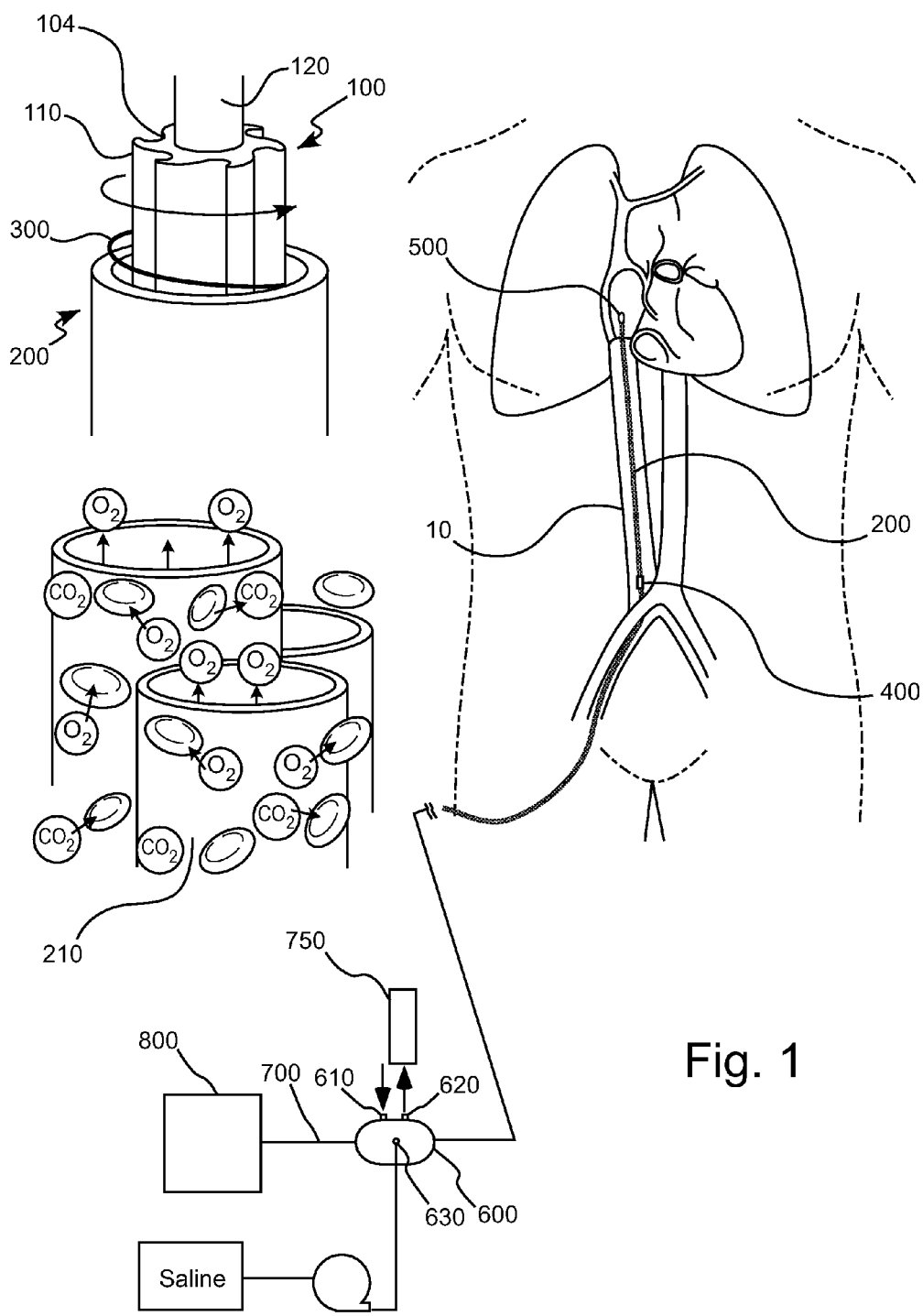
FIG. 1 illustrates insertion of an embodiment of an intravascular device of the present invention through the femoral vein for placement in the vena cava.
Figure 4:
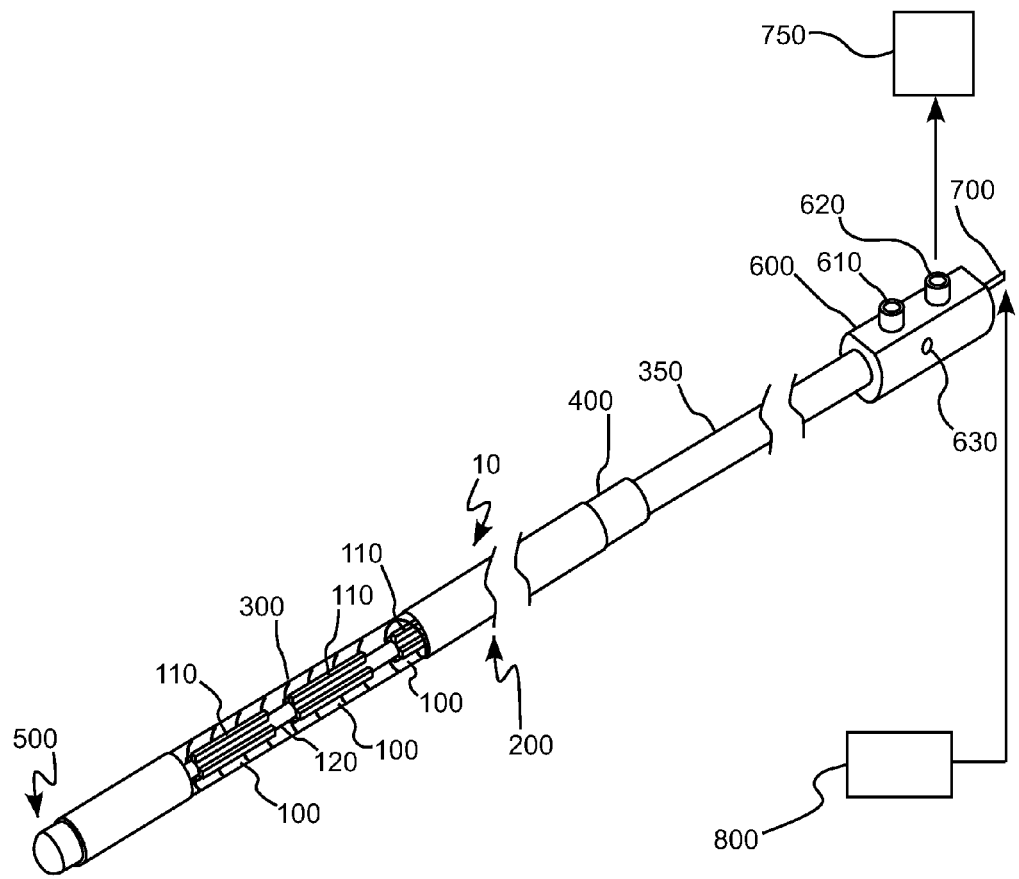
FIG. 4 illustrates a perspective view of an embodiment of an intravascular device of the present invention.
Figure 5A:
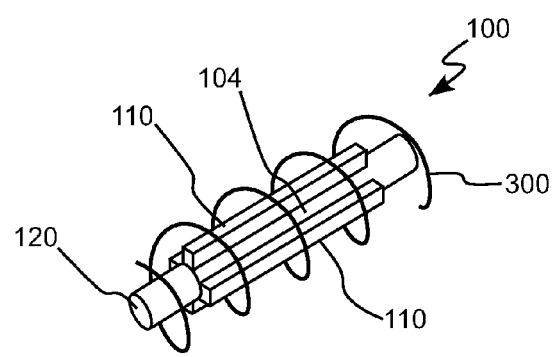
FIG. 5A illustrates an enlarged view of an impeller unit of the device of FIG. 4A positioned upon the impeller shaft of the device of FIG. 4.
Figure 5B:
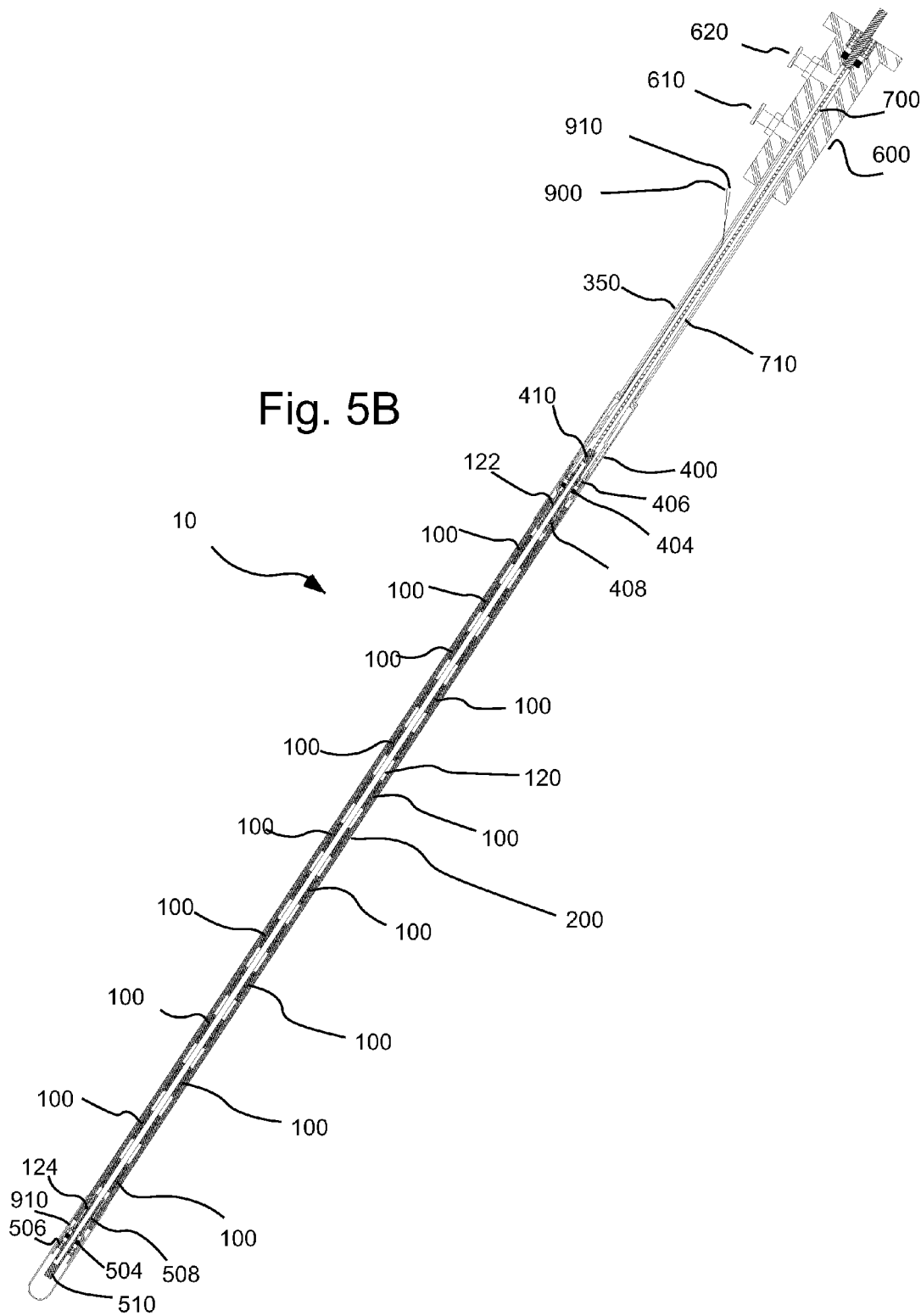
FIG. 5B illustrates a cross-sectional view of the device of FIG. 4.
Figure 5C:
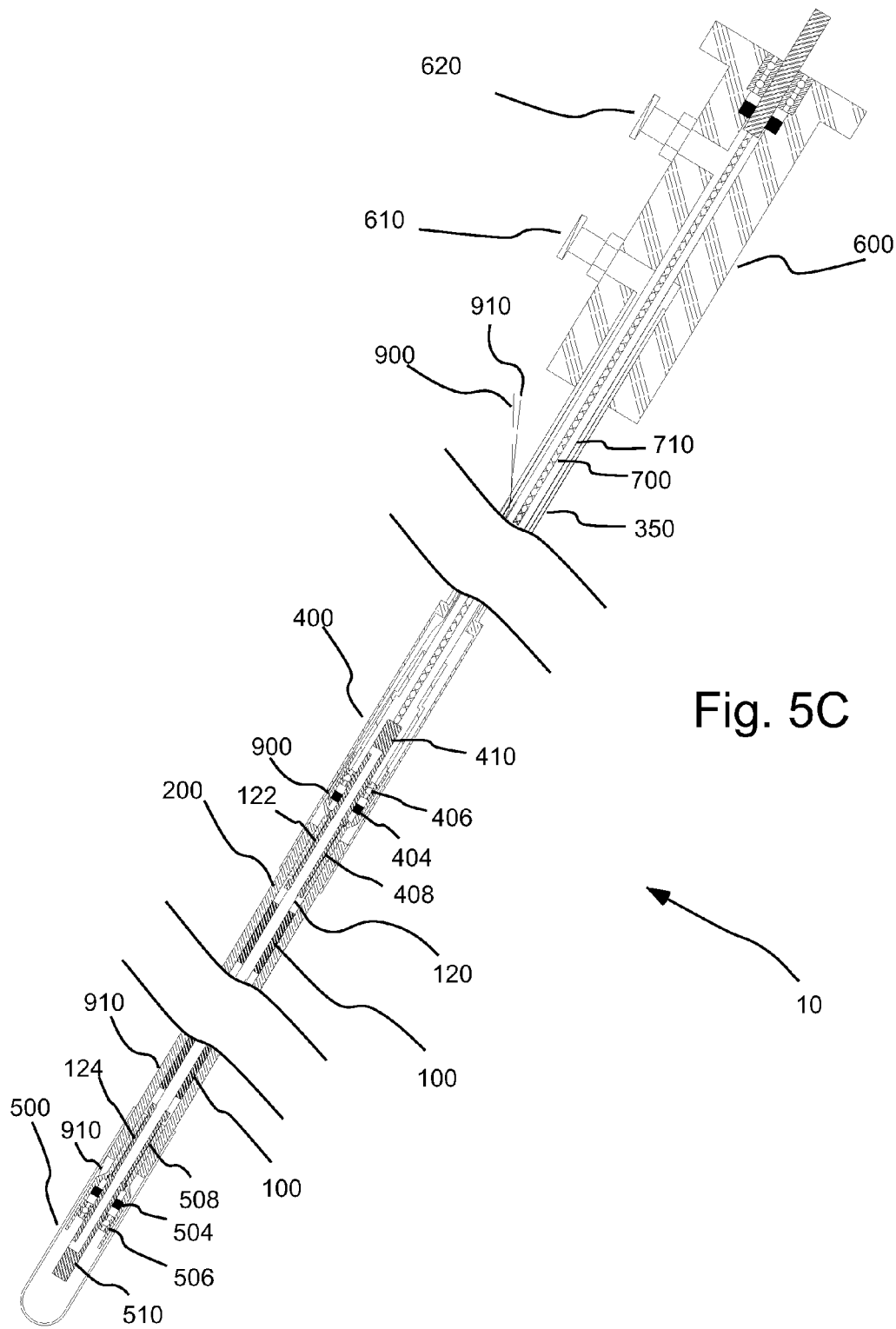
FIG. 5C illustrates an enlarged cross-sectional view of the device of FIG. 4.
Figure 5D:
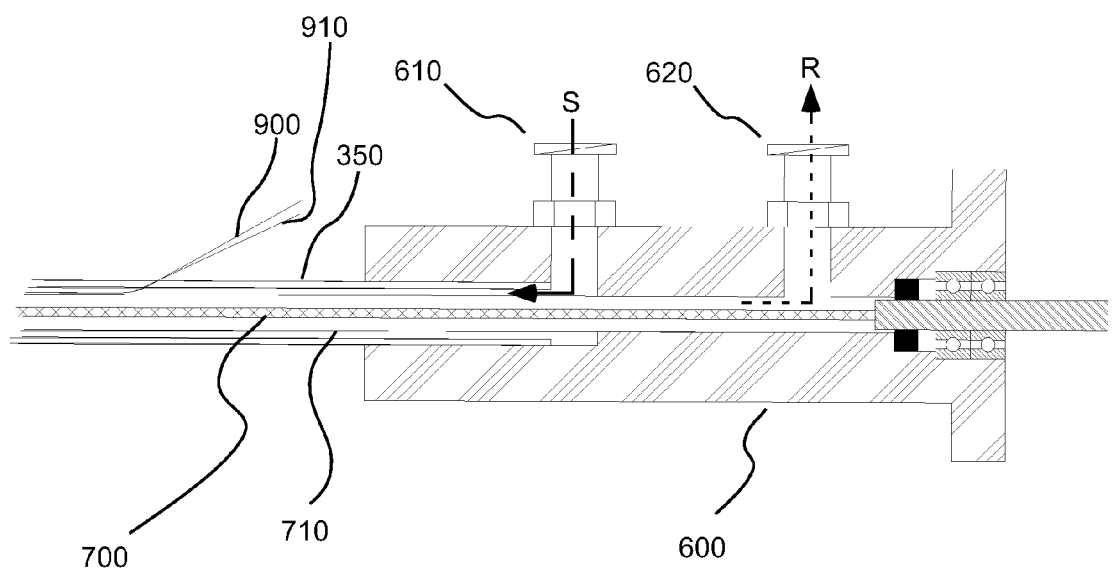
FIG. 5D illustrates an enlarged cross-sectional view of a proximal manifold of the device of FIG. 4.

The devices of the present invention can, for example, be inserted through the femoral vein for placement in the vena cava in the manner of a catheter to actively process venous blood as illustrated in FIG. 1. In several embodiments, the devices of the present invention include a gas exchange membrane system including, for example, a plurality of hollow fiber membranes (HFM), sometime referred to herein as a HFM bundle, that supplement oxygenation and carbon dioxide removal through diffusional processes as illustrated in FIGS. 2A through 3.

In general, the intracorporeal devices and systems of the present invention can be of reduced size when compared to previous devices designed for intravascular respiratory assist, which facilitates percutaneous insertion. Reduction in the size, however, can limit available membrane (for example, HFM) surface area. In a number of embodiments, efficiency in removal of $CO_2$ per unit membrane surface area is improved to offset limits in available surface area. Furthermore, oxygen ($O_2$) transfer rates per unit surface are also improved as compared to currently available intracorporeal and other devices. In several embodiments of the devices of the present invention, agitation elements or mechanisms such as rotating elements, impellers or rotors (sometimes referred to herein collectively as impellers) are positioned within a stationary HFM bundle to impel flow or create forced flow within and through the HFM bundle to increase efficiency of gas exchange per unit surface area. Internalization of rotational components within the HFM bundle of the devices of the present invention assists in protecting the surrounding tissue from damage.

Devices of the present invention were evaluated in vitro and in vivo to assess design and performance. Acceptable hemolysis levels were observed with high-speed rotational impellers within HFM bundles. Standard gas exchange characterization tests in, for example, deionized or DI water showed an increase in $CO_2$ removal efficiency and $O_2$ transfer/exchange as compared to previously disclosed percutaneous respiratory assist devices or oxygenators. Several embodiments of devices of the present invention were evaluated in a bovine model and an average efficiency of 513±20 ml $CO_2$/min/m$^2$ was attained at 20,000 RPM.

As described above, membrane oxygenators employ hollow fiber membrane (HFM) technology to achieve gas transfer. The HFMs can, for example, be made from polymers such as polymethylpentane or polypropylene that are extruded or otherwise formed into microporous tubes. The miniature tubes can further be arranged into bundles that are used in a number of currently available oxygenators. FIGS. 2A and 2B displays a magnified view of HFMs. Wall porosity enables the membranes to exchange oxygen and carbon dioxide gases while blood flows external to the fibers. The walls of the fibers are hydrophobic and prevent fluid from leaking into the lumens.

The process driving gas exchange in HFM is diffusion. Oxygenators can, for example, be setup to process venous blood that is high in carbon dioxide ($CO_2$) concentration and low in $O_2$ concentration. Gas rich in oxygen or pure oxygen ($O_2$) gas is passed through the HFM lumens at a pressure (for example, $pO_2 \approx 740$ mmHg) that is greater than the gas tension/partial pressure of oxygen in the blood. A transmembrane concentration gradient is thus created between venous blood ($pO_2$=38 mmHg, $pCO_2$=45 mmHg) and fiber lumen. The high concentration of $CO_2$ in the blood favors diffusion into the low concentration side within the HFM lumen, and conversely the high concentration of $O_2$ in the HFM favors diffusion into the low concentration blood-side. A schematic representing $CO_2$ diffusion through a hollow fiber membrane is shown in FIG. 3. Blood passing through the HFM bundle is thus supplemented with oxygen and removed of carbon dioxide in a fashion similar to the natural lung.

During insertion, the devices or catheters of the present invention can, for example, extend through the femoral vein into the vena cava to span the right atrium of the heart. FIG. 1 illustrates insertion of a device 10 of the present invention within the vena cava prior to reaching a position spanning the right atrium. A position spanning the right atrium allows the device to process all venous blood returning from the major vessels of the body. Furthermore, flow from the vena cava into the right atrium creates an additional blood mixing component since cross-flow will occur. This mixing regime may influence boundary layer formation.

Pure oxygen gas can, for example, be shuttled through the HFM bundle under a vacuum so that $O_2$ transport occurs by diffusion only. The vacuum assists in ensuring that oxygen sweep gas is not bubbled through the pores of the HFM into the blood as a result of a high transmembrane pressure gradient. In several embodiments described in further detail below, manifolds at the proximal and distal ends of the fiber bundle collectively organize the fibers to permit sweep gas flow in parallel through the bundle. Conduits in fluid connection with the manifolded bundle create a single, continuous flow path for sweep gas. Flowrate through the device can, for example, be maintained approximately 40-60 times greater than the $CO_2$ exchange rate to maximize efficiency. See, for example, Federspiel W J, Hattler B G: Sweep gas flowrate and $CO_2$ exchange in artificial lungs. *Artif Organs* 20: 1050-1052, 1996, the disclosure of which is incorporated herein by reference. Lower flowrates can lead to $CO_2$ accumulation within the HFMs which reduces the gas concentration driving gradient responsible for diffusion. The flowrate range set forth above assists in assuring that gas transfer is maximized and not dependent upon sweep gas flowrate.

Preferably, the devices of the present invention are operable without causing harmful effects to the blood. In that regard, actively mixing the blood can cause hemolysis if erythrocytes experience excessive shear stresses and exposure times. In several embodiments, the devices of the present invention were designed (but not optimized) to minimize hemolysis (for example, as determined by maintaining acceptable blood plasma free hemoglobin (PFHB) levels).

As described above, in reducing the insertion size of the catheter, there is a resultant loss in HFM surface area. In the devices of the present invention, a novel active mixing approach is incorporated to reduce concentration boundary layers to counterbalance the loss of HFM surface area and provide acceptable overall gas exchange. In several embodiments, at least one rotating impeller unit was positioned within the HFM bundle to distribute fluid through the bundle. The impeller units were designed so that the HFM bundle would remain stationary and enclose the rotating components.

Gas exchange tests were first performed to evaluate gas exchange efficiency. The tests were further subdivided to analyze the effects of impeller geometry on gas exchange in both the standard deionized (DI) water solution and a blood representative viscous solution. Tortuous loop tests were implemented in early stages to ensure mechanical operation in severe bending environments. Fatigue tests were conducted in bovine blood to assess hemolysis. The devices of the present invention were also tested in four acute calf studies to examine gas exchange between different impeller geometries.

One embodiment of a device 10 of the present invention is illustrated in FIGS. 4 through 7B. Device 10 includes a plurality of spaced internal impeller units or elements 100 capable of rotating at, for example, 20,000 RPM to impart fluid motion and to force fluid radially outward. In the embodiment as illustrated, for example, in FIGS. 4 and 5A, impeller units 100 included four flat vanes 110 extending radially outward from a common cylindrical base 104 which was positionable on flexible impeller shaft 120. The impeller system can also be described as a single agitation or impeller system including a plurality of groups of vanes that are axially spaced on shaft 120. An HFM bundle 200, as described above, enclosed rotating impeller units 100. In the illustrated embodiment, HFM fabric 200 was formed around a support 300 in the form of, for example, a stainless steel spring or helical coil. In several devices 10 studied in the present invention, a 5 mm diameter cavity existed within stent or spring 300 to create a hollow bundle module for impeller units 100 to reside. Spring 300 served as both a backbone or support to support HFM fabric/HFM bundle 300 and as a barrier to shield HFM bundle 300 from rotating vanes 110 of impeller, even in tortuous configurations. Support 300 was secured to a medial manifold 400 and a distal manifold 500 and stretched to provide ample spacing for fluid passage. As illustrated in, for example, FIG. 5B, in several studied embodiments, HFM bundle was approximately 30 cm in length and 12 to 14 (14 in the illustrated embodiment) impeller units 100 were positioned along shaft 120 with a spacing of approximately 0.5 inches therebetween. In several studied embodiments of device 10, CELGARD® ARX30-240 hollow fiber membrane fabric (Celgard, Inc., of Charlotte, N.C.) was used as fiber bundle 200. Characteristics of the individual HFMs and the HFM bundle studied are set forth in Table 1.

TABLE 1

| ARX30-240 HFM | | HFM Bundle | |
|---|---|---|---|
| Material | Polypropylene | Bundle Length (cm) | 30 |
| Outer Diameter (μm) | 300 | Outer Diameter (mm) | 8 |
| Inner Diameter (μm) | 240 | # of Fibers | 250 |
| Average Pore Size (μm) | 0.03 | Fiber Layers | 4 |
| Porosity (%) | 40 | Wefts | none removed |
| Fibers per Inch (FPI) | 54 | Surface Area (m$^2$) | 0.07 |

Hollow fiber membranes in artificial lungs (blood oxygenators or respiratory assist devices) are typically made using polyolefin polymers, with polypropylene, polyethylene and polymethylpentene being commonly used materials. The hollow fiber membranes are created by extrusion or other manufacturing processes to create a microporous fiber wall with sub-micron sized pores spanning the walls. These microporous fibers are adequate in commercial blood oxygenators for short term blood contact. In respiratory assist devices and artificial lungs required for longer-term blood contact (>6 hours), the microporous fibers can leak plasma into the fiber lumens and create a problem known as plasma wetting. To prevent or retard plasma wetting, composite or asymmetric microporous hollow fiber membranes can be used in the devices and systems of the present invention. A composite HFM is a standard microporous hollow fiber membrane on which a thin coating of a nonporous, permeable polymer is applied. As the nonporous coating should be very gas permeable, the coating is often made from a highly gas permeable polymer such as siloxane polymers. An asymmetric microporous hollow fiber membrane is one in which the fiber wall is fabricated so that the porosity varies across the wall and goes to zero at the fiber surface. The pores are then essentially sealed by the same gas permeable material from which the fiber is made.

Studied devices 10 were designed so that impeller units 100 could be easily interchanged to rapidly evaluate different impeller geometries. Impeller units 100 were mounted directly to impeller shaft 120 via adhesive. Fiber bundle 200 was constructed from 300 μm OD fibers 210 (see FIG. 1) in fabric form, with fibers 210 potted into medial manifold 400 and distal manifold 500. In that regard, epoxy was applied to fiber bundle 200 to fix manifolds 400 and 500 to bundle 200.

Distal manifold 500, medial manifold 400 and a proximal manifold 600 operated, in part, to separate gas pathways in device 10. Proximal manifold 600 was used to introduce, for example, oxygen sweep gas via an inlet port 610 and also included an outlet port 620 for exhaust gas removal. Oxygen gas was introduced into inlet port 610 of proximal manifold 600 and directed through HFM bundle 200. Distal manifold 500 redirected exhaust gas back through impeller tubing 120 towards proximal outlet port 620. Proximal manifold 600 also operated to couple a device drive line 700 to a drive system such as a servomotor drive system 800. As described in more detail below, medial manifold 400 and distal manifold 500 included bearings and seals to stabilize rotation and prevent fluid entry into device 10. Manifolds 400, 500 and 600 were stationary during operation, thereby providing a base to attach support 300 and HFM bundle 200. Flow through the device was driven by a vacuum pump 750 connected to the proximal manifold outlet port 620. Drive system 800, including a DC servomotor and an amplifier, provided the required torque to actuate and control drive line 700.

In the illustrated embodiment, the sweep gas flowed into (via inlet port 610) and through a flexible pneumatic shaft or tube 350 (fabricated, for example, from a polymer such as polyurethane) and into medial manifold 400. Drive line 700 passed through a conduit 710 which was positioned within tube 350. As illustrated by arrow S in FIG. 5D, inflowing sweep gas flowed in an annular passage between conduit 710 and the inner wall of tube 350. At medial manifold 400, the sweep gas (represented by arrows S in, for example, FIGS. 6C and 6D) was distributed into a first end of hollow fibers 210 of hollow fiber bundle 200. Upon exiting a second end of hollow fibers 210, the sweep gas was collected within distal manifold 500. In distal manifold 500, the returning sweep gas (represented by arrows R) entered a fluid path within a connector 510 rotatably positioned within distal manifold 500. Returning sweep gas passed from connector 510 into a central fluid path within impeller shaft 120, with which connector 510 was in operative and fluid connection.

Figure 6A:
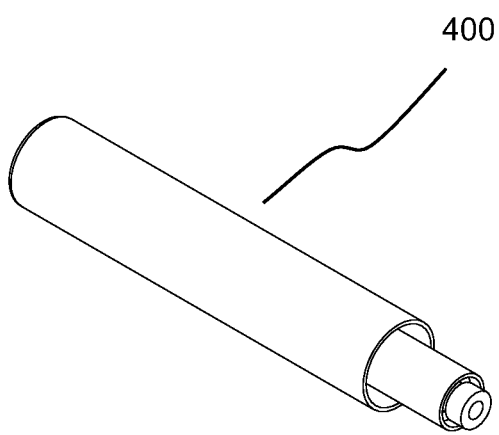
FIG. 6A illustrates a perspective view of the medial manifold of the device of FIG. 4.
Figure 6B:
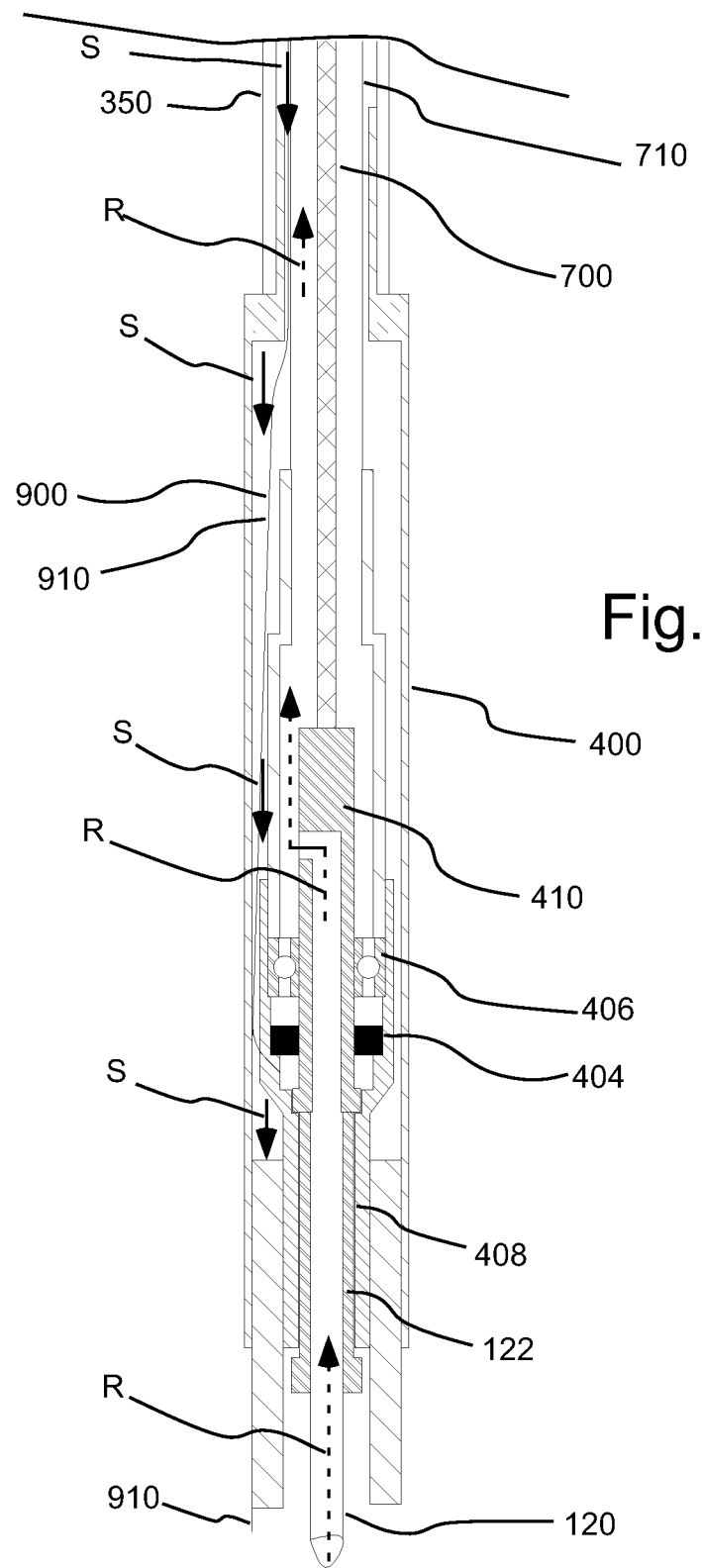
FIG. 6B illustrates an enlarged cross-sectional view of the medial manifold.
Figure 6C:
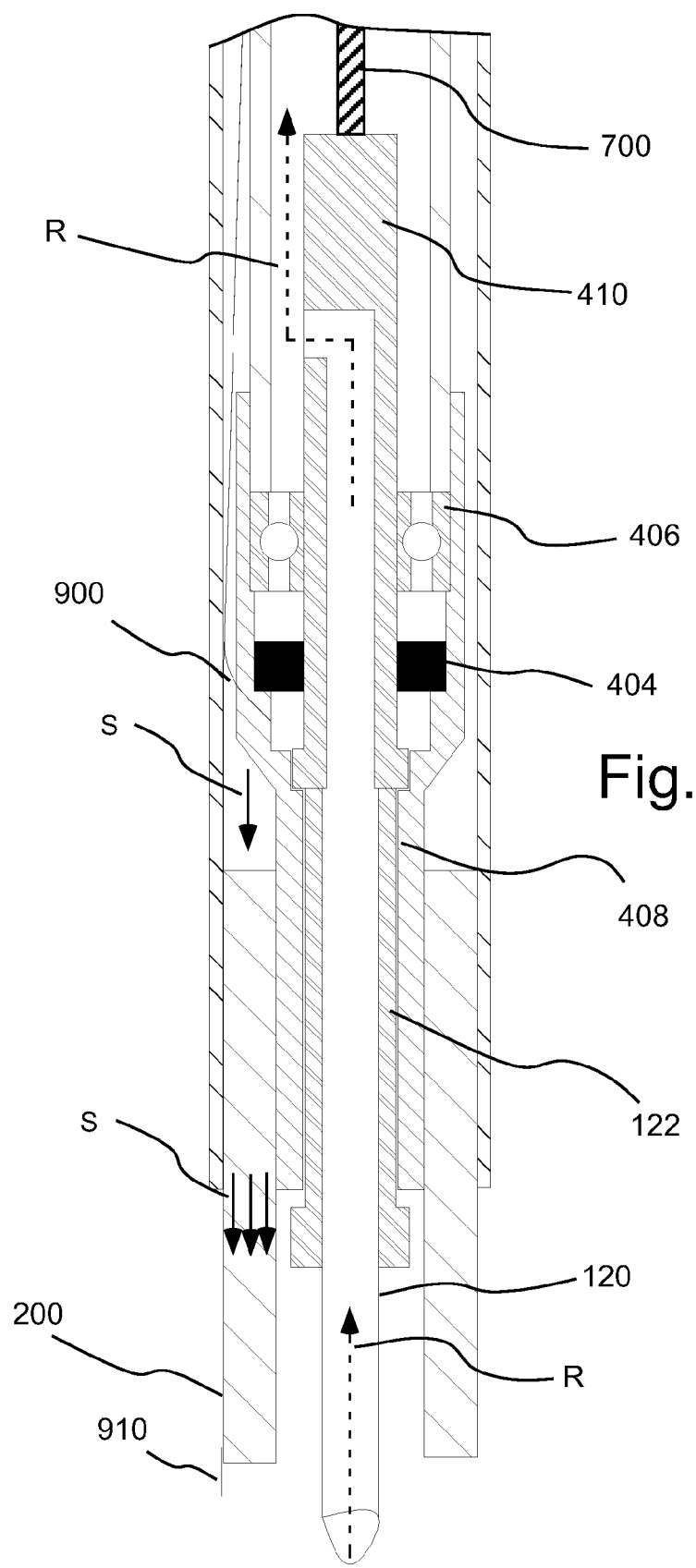
FIG. 6C illustrates another enlarged cross-sectional view of the medial manifold.
Figure 6D:
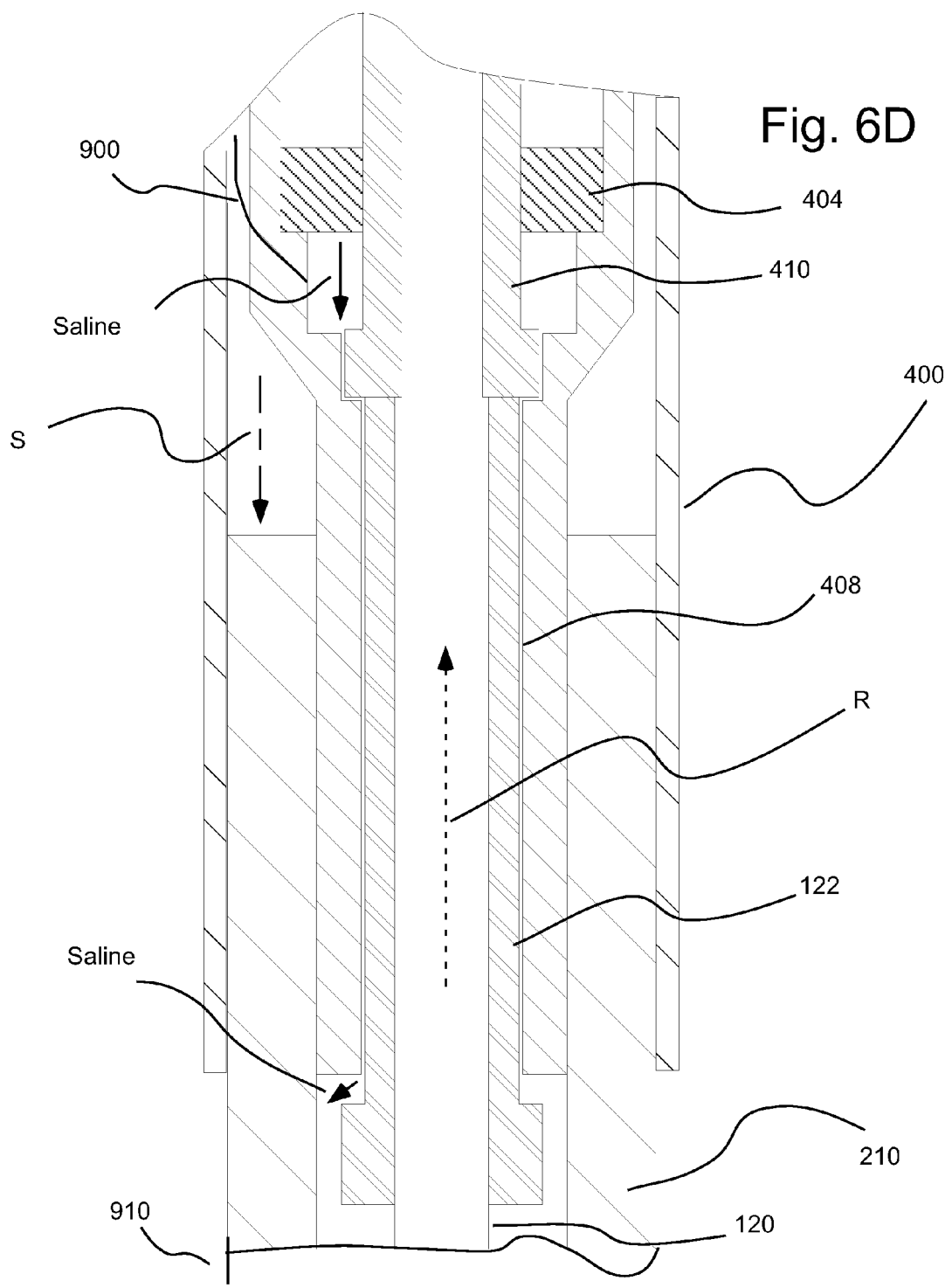
FIG. 6D illustrates another enlarged cross-sectional view of the medial manifold.

The returning sweep gas passed through the center of device 10 (within the central fluid path within impeller shaft 120) back to medial manifold 400 as, for example, illustrated in FIGS. 6C and 6D. In that regard, impeller shaft 120 was in operative and fluid connection with a distal end of a connector 410 rotatably positioned within medial manifold 400. Drive line 700 was in operative connection with a proximal end of connector 410 and imparted rotational motion to connector 710 and thereby to impeller shaft 120. From medial manifold 400, returning sweep gas passed through an annular space between drive line 700 and an interior wall of conduit 710 to proximal manifold 600. The returning sweep gas exited device 10 by flowing through conduit 710 to outlet 620 of proximal manifold 600 as, for example, illustrated in FIG. 5D.

Once again, a negative pressure gradient (created, for example, via a sealed vacuum) was used to drive oxygen flow from inlet port 610 to exhaust gas outlet 620. The sweep gas flowrate requirement for a prototype exchanging 75 ml $CO_2$/min was determined to be at least 3 LPM using the 40-60 multiplier discussed above. The main resistance to flow in device 10 was the HFM bundle and the resistance was estimated according to the following equation assuming oxygen to be a compressible gas:

$$P_o^2 - P_L^2 = 2\left(\frac{128\,\mu L}{N\pi d^4}\right)P_{atm}Q^{RTP} \quad (1)$$

where $P_o$ is upstream pressure, $P_L$ is downstream pressure, $\mu$ is gas viscosity, L is fiber length, N is total number of fibers, d is fiber inner diameter, $P_{atm}$ is atmospheric pressure, and $Q^{RTP}$ is sweep gas flowrate (LPM). For a flowrate of, for example, 3.5 LPM, the corresponding pressure drop over the bundle was approximately 50 mmHg. See Eash H J, Frankowski B J, Hattler B G, Federspiel W J: Evaluation of local gas exchange in a pulsating respiratory support catheter. *Asaio J* 51: 152-157, 2005, the disclosure of which is incorporated herein by reference. Vacuum pump 750 was capable of producing 9 LPM flow at this pressure head, and therefore the bundle design was adequate to attain sufficient sweep flow.

High-speed electromechanical drive system 800 included a brushless DC-servomotor (Series 2444-024B, MicroMo Electronics Inc. of Clearwater, Fla.) and 2-quadrant PWM servo amplifier (Series BLD 3502, MicroMo Electronics Inc.) and provided rotation and control. A conditional analog voltage of 0-5 volts set by a potentiometer dictated motor speed. The unit was powered by a 24 volt AC/DC quad output power supply (Series NFS110-7602P, Artesyn Technologies, Inc. of Boca Raton, Fla.). The components were housed within a single box for ease of use and protection from electrical failure. Drive system 800 included a mini DC cooling fan to remove heat from the power supply. Motor speed was measured with a digital rate indicator (Model CUBS, Red Lion Controls of York, Pa.). A wire connection was introduced to the amplifier to tap voltage pulses returning from the servomotor hall-sensors. Connection from the amplifier to the digital rate indicator enabled pulses to be counted and displayed. A mechanism for measuring motor torque was also included in the setup. The torque generated by the servomotor was directly proportional to the current requirement for motor operation. A wire connection was made to directly measure the DC current output from power supply to amplifier. The measurement was representative of the supplied current from amplifier to motor and was used to calculate motor torque by the servomotor torque constant. Finally, a fuse was placed in series from power supply to amplifier. The fuse automated the system to shutdown upon motor stall and protected the motor from damaging current levels.

As discussed above, each of medial manifold 400 and distal manifold 500 included a seal and a bearing to, for example, prevent blood intake and to support concentric impeller rotation. A diamond like carbon coating (DLC) can, for example, be employed where the rotating shaft and the seals make contact to, for example, reduce the coefficient of friction and add lubricity. Medial manifold 400 is illustrated in, for example, FIGS. 6A through 6D. A rotary seal 404 manufactured from nitrile rubber (#711800, Chicago Rawhide/SKF USA, Inc. of Elgin, Ill.) was used in the studied embodiments. Seal 404 accommodated shaft diameters of 0.110"-0.140" and had an outer diameter of 0.313 inches. Seal 404 was modified to an outer diameter of 0.250 inches to meet size specifications. Seal 404 was also configured with a shielded, mini ball bearing 406 (#35380815, MSC Industrial Supply Co. of Melville, N.Y.) possessing a 0.125 inches shaft diameter and 0.250 inch outer diameter. In several studied embodiments, a generally cylindrical sleeve of material 408 (such as VESPEL®, a polyamide based polymeric material available from DuPont) was positioned within the housing of medial manifold 400 adjacent to the distal or blood-side face of seal 404. Material 408 was 0.5 inches in length and had an inner diameters of 0.113 inches. That diameter created a 0.0005 inch clearance between a connector section 122 of impeller shaft 120 and material 408.

Figure 7A:
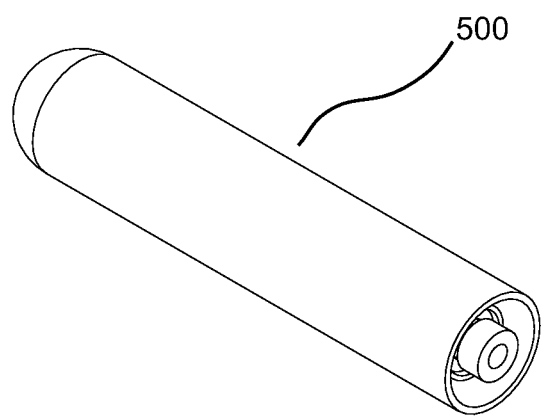
FIG. 7A illustrates a perspective view of the distal manifold of the device of FIG. 4.

Distal manifold 500 is illustrated in FIGS. 7A and 7B. As with medial manifold 400, a rotary seal 504 fabricated from nitrile rubber (#711800, Chicago Rawhide/SKF USA, Inc.) was used. Seal 504 accommodated shaft diameters of 0.110"-0.140" and had an outer diameter of 0.313". Seal 504 was modified to an outer diameter of 0.250 inches to meet size specifications. Seal 504 was also configured with a shielded, mini ball bearing 506 (#35380815, MSC Industrial Supply Co.) having a 0.125 inch shaft diameter and 0.250 inches outer diameter. As described above in connection with generally cylindrical sleeve of material 408, a generally cylindrical sleeve of material 508 (VESPEL) was positioned within the housing of distal manifold 500 adjacent to the proximal or blood-side face of seal 504. As was also the case with material 408, material 508 was 0.5 inches in length and had an inner diameters of 0.113 inches. The diameter created a 0.0005 inch clearance between a connector section 124 of impeller shaft 120 and material 508.

In several studied embodiments of device 10, the selected material for flexible impeller shaft 120 was wire reinforced PEBAX® (a polyether block amide available from Arkema France Corporation of Colombes, France) catheter tubing (#N98-TOL-664, available from New England Wire Technologies of Lisbon, N.H.). The tubing was chosen from several samples based on tortuous loop test results discussed in Appendix A. Impeller shaft 120 was operatively connected to drive shaft or drive line 700 via connector 410 as described above, which was produced from an internal component of bi-directional 0.072 inch diameter shaft (#067N133C, S.S. White Technologies of Piscataway, N.J.) that was coupled to servomotor system 800 via proximal manifold 600 as also described above.

Figure 8B:
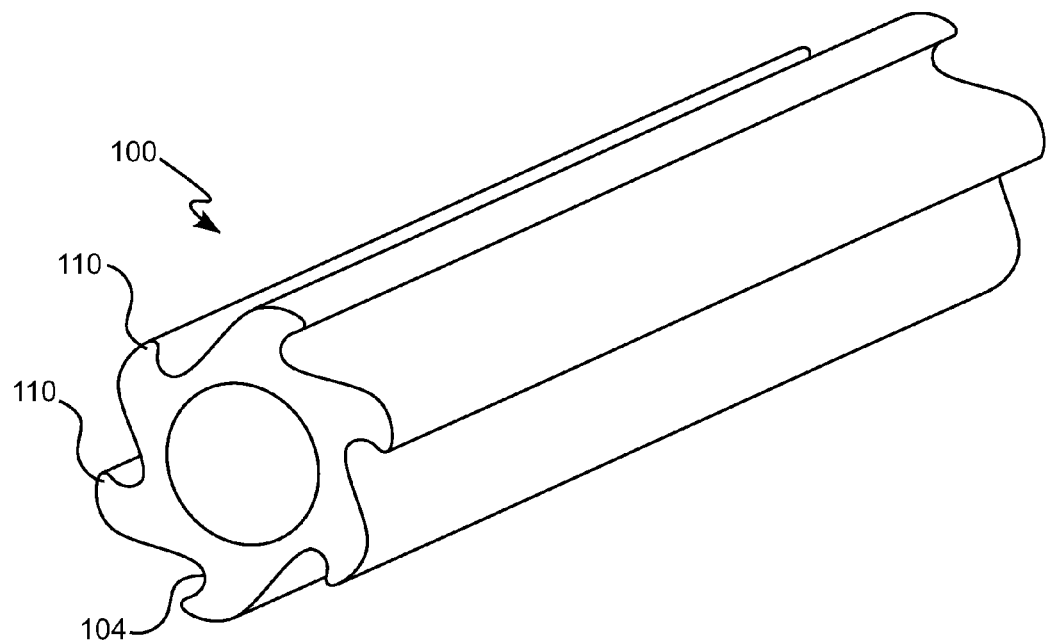
FIG. 8B illustrates an enlarged perspective view of a sawtooth embodiment of an impeller unit of the present invention.
Figure 8C:
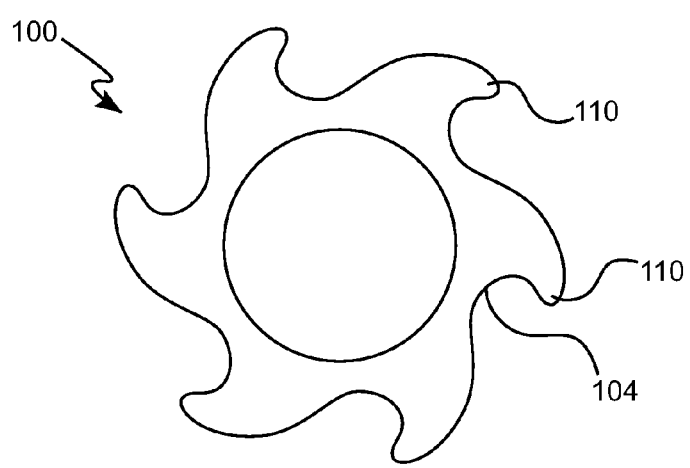
FIG. 8C illustrates an enlarged front view of a sawtooth embodiment of an impeller unit of the present invention.

Tortuous loop tests described in the Experimental Section hereof demonstrated that 0.5 inch length impeller units 100 with 0.5 inches spacing therebetween upon flexible impeller shaft 120 were suitable to attain desired impeller flexibility. Moreover, the spacing between impeller units 100 can promote recirculating flow from impeller segments into non-impeller regions and thereby promote gas exchange. Various impeller/vane units 100 evaluated in device are shown in FIGS. 8A(1) through 8A(9). Enlarged illustrations of a sawtooth impeller unit 100 of the present invention are set forth in FIGS. 8B and 8C. A cylindrical blank was also made as a control and is not displayed. Paddle and axial impeller units were fabricated in-house. Axial units were produced by turning static mixers (#04667-18, Cole Parmer Instrument Co. of Vernon Hills, Ill.) on a lathe to a 0.152" outer diameter. Other impeller units 100 were produced by SLA rapid prototyping. 2-flat, 4-flat, sawtooth, paddle, centrifugal and cone were developed as radial units. The RAX vanes included a combination of radial and axial geometries to assist in carrying fluid to the radial blades of the unit. All studied impeller units 100 had inner diameters of 0.084 inches, outer diameters of 0.156 inches, and lengths of 0.5 inches.

WATERSHED™ 11120 stereolithography resin available from DSM Somos of Elgin, Ill. was used for impeller unit manufacture. The material was compatible with SLA prototyping and also resistant to water adsorption/swelling. Limited clearance within the cavity within HFM bundle 200 made water resistance a desirable property. Once again, materials/sleeves 408 and 508 were made from DuPont VESPEL; which has demonstrated applicability as a low wear material which absorbs very little water. Drive components, medial manifold 400 and distal manifold 500 were fabricated from 316 stainless steel on a Hardinge lathe. Proximal manifold 600 was formed from acrylic polymer. Inlet and exhaust tubings were made of polyurethane plastic. Component mating was accomplished using the 2:3 polycin to vorite epoxy or PERMATEX® clear RTV silicone adhesive sealant (available from Permatex, Inc. of Hartford, Conn.). Mechanical drive parts were connected using silver solder.

Initial evaluations of a number of devices 10 including PEBAX tubing for impeller shaft 120 in an animal model revealed mechanical failures of such an impeller shaft 120. Prototype dissections also showed accumulations of paste-like blood constituents in the external (blood side) materials/sleeves 408 and 508 that were believed to cause variations in friction, ultimately resulting in the tubing failure. The annular space between connector sections 122 and 124 and material/sleeves 408 and 508, respectively, may, for example, have undesirably served as a pathway through which blood traveled to contact seals 404 and 504. In that regard, the blood may have penetrated the external housing prior to contacting seals 404 and 504. Shear stress calculations estimated a stress exposure of 5,000 dynes/cm$^2$ at 20,000 RPM (Appendix B.1). Paul et al. found the shear stress threshold for hemolysis to be 3750 dynes/cm$^2$ and 4250 dynes/cm$^2$ at exposure times of 1.4 and 0.425 seconds respectively. Paul R, Apel J, Klaus S, Schugner F, Schwindke P, Reul H: Shear stress related blood damage in laminar couette flow. *Artif Organs* 27: 517-529, 2003, the disclosure of which is incorporated herein by reference. The shear stress level was thus possibly causing hemolysis and contributing to the accumulation of blood constituents.

The PEBAX tubing also experienced non-uniform rotation between medial manifold 400 and distal manifold 500 that created torsional stresses along the tubing length. The combination of high-speed and torque caused the PEBAX tubing to fail in two ways: either the tubing completely ruptured leaving a helical pattern in the direction of motor rotation, or the hollow tubing collapsed on itself with the same observed pattern. The pattern indicated a delay or complete seizure in impeller angular velocity in the distal manifold causing the tubing to overturn.

Given the failure of PEBAX tubing for impeller shaft 120 in several studies, a concurrent effort was undertaken to prevent blood thrombosis and improve impeller tubing strength. A flushing fluid (for example, heparinized saline) purge of seals 404 and 504 and exterior (blood-side) annular spaces between connector sections 122 and 124 and materials/sleeves 408 and 508, respectively, was implemented within medial manifold 400 and distal manifold 500, respectively, to prevent thrombus and blood damage. The purge benefited device 10 three-fold by: (1) impeding blood penetration into the annular spaces adjacent connector sections 122 and 124, (2) preventing direct blood contact with seals 404 and 504, and (3) removing friction-generated heat from seals 404 and 504.

To implement a saline purge, orifices were drilled into medial manifold 400 and distal manifold 500 to deliver the saline to the exterior face of the seals 404 and 504 and flush through the annuli between materials/sleeves 408 and 505 and connector sections 122 and 124, respectively. As, for example, illustrated in FIGS. 5D and 6D, two 304 stainless steel hypo tubing lines 900 and 910 (#HTX-25R-24, Small Parts Inc. of Logansport, Ind.) with IDs of 0.010" and ODs of 0.020" were passed through tubing 350 to enter the annular path between conduit 710 and tubing 350. Alternatively, saline (and/or other flushing fluid(s)) can enter device 10 via a saline port 630 formed in proximal manifold 600 (see FIG. 4), which can, for example, be in fluid connection with one or more delivery conduits such as hypo tubing lines 900 and 910. In the studied embodiments, hypo tubing line 900 connected to medial manifold 400 to deliver saline. Hypo tubing line 910 passed through medial manifold 400 and along the exterior of HFM bundle 200 to connect to proximal manifold 500. Sufficient saline pressure (for example, at least 200 mmHg) was used to prevent blood seepage. Using a pressure of 200 mmHg as a guideline, the flowrate of saline through a single annular space to generate the pressure standard was calculated to be 12 ml/hr (see Experimental Section (B.2.)). A minimal saline flowrate of 12 ml/hr was used in all studies.

A controlled volume of flushing fluid or liquid (saline/heparin) was thus introduced into an engineered space (the annular space between materials/sleeves 408 and 508 and connector sections 122 and 124, respectively) between the blood and seals 404 and 504. As discussed above, this space was approximately 0.5 Inches long, and there was an approximately 0.0005 inch gap between the sleeves/seal housings and the rotating impeller shaft connector sections. The flushing fluid entered into the bearing seal housing of the manifolds on the external side (or blood side) of seals 404 and 504 and traveled through the engineered gap wherein it purged/prevented inflow of blood. This space acted as a barrier between the blood and the seals and rotating components. The flushing fluid purge minimized or eliminated contact between blood and rotating components that cause thrombus and blood damage by heat or friction generated at the interface of a rotating shaft and the seal. The flushing fluid/saline also provided lubrication and cooling to the shaft-seal interface.

To improve impeller shaft strength, a stainless steel coil (#HVT18642-01, available from Heraues Vadnais Inc. of Saint Paul, Minn.) was used in several studies for impeller shaft/tubing 120. The coil included 4-filar units that served to individually distribute torque loads. The coil was made to dimensions of 0.060" ID and 0.083" OD from 0.010" 304 stainless steel wire wound in a clockwise direction. This embodiment of impeller tubing 120 was formed as a hollow flexible drive shaft and could transmit higher loads than plastic tubing. PEBAX heat shrink tubing (#P2-140-006-CLR, available from Cobalt Polymers of Cloverdale, Calif.) with a wall thickness of 0.006" was applied to the coil to produce the finalized, sealed tubing used in devices 10. Impeller shaft 120 was tested in a torsion testing apparatus. Impeller shafts 120 formed from stainless steel coil achieved much larger torsional deflections prior to failure than the previously studied PEBAX tubing and were integrated into device 10 for further studies. Although the stainless steel coil embodiment of impeller shaft 120 exhibited greater strength than the PEBAX tubing embodiment, shear stresses were decreased sufficiently via use of a flushing fluid purge as described above, that the PEBAX tubing embodiment of impeller shaft 120 could have been implemented without failure when used in connection with such a purge.

As described above, various impeller units 100 geometries were evaluated in bench studies, which were followed by studies in a bovine model. Gas exchange tests of devices 10 were conducted in vitro to assess gas exchange efficiencies with the various impeller units 100. Devices 10 were tested in the standard DI water and a viscous solution similar to blood to provide insight regarding impeller geometry performance.

Figure 9A:
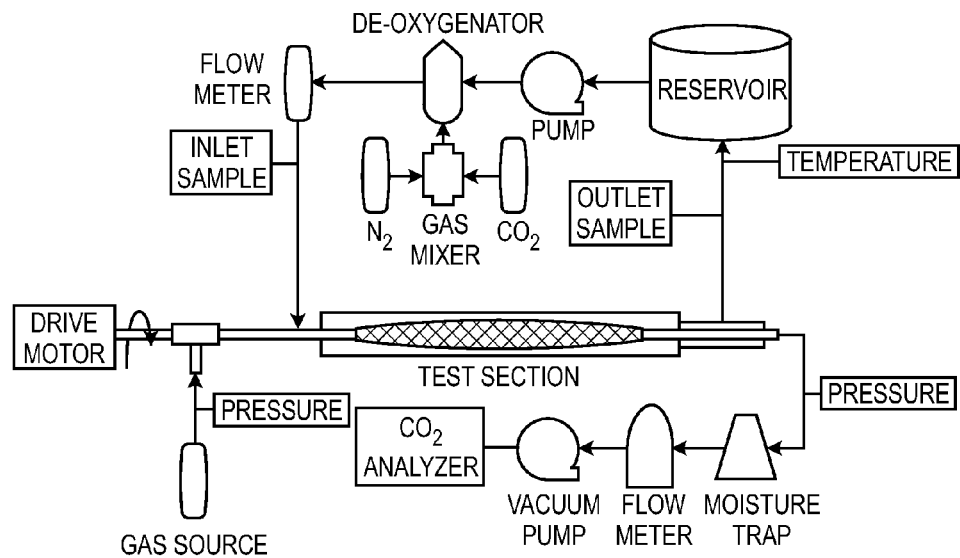
FIG. 9A illustrates an experimental setup for studies of gas exchange efficiency of devices of the present invention.

The in vitro test was an idealized simulation of the vena cava environment and provided rapid device characterizations allowing device to device comparisons and indication of trends that could be observed in vivo. Testing was performed by introducing the device into separate fluid and gas circuits. The fluid loop re-circulated de-ionized water past the device. Water was thus the blood representative fluid and served as the gas carrying medium. Device 10 was placed in the fluid circuit within a ⅞" diameter acrylic test section that simulated the vena cava. The fluid circuit contained a reservoir, fluid pump, thermometer, heater, flow meter, pressure transducer and de-oxygenator, and all were connected with standard laboratory TYGON® tubing (plastic tubing) available from Saint-Gobain Performance Plastics Corporation of Aurora, Ohio. A schematic of the test setup is illustrated in FIG. 9A.

The de-oxygenator was used to establish test section water inlet conditions. Conditions set were a $pO_2$ of 25-35 mmHg and a $pCO_2$ of 47-53 mmHg, which represented physiological normocapnia venous blood. The water conditions were monitored on an ABL 555 soluble gas analyzer machine. Water flowrate through the loop was maintained at 3 LPM with a temperature of 37° C., and the water gauge pressure within the test section was maintained at approximately 10 mmHg. No micro-bubble formation was observed.

The gas circuit established the pathway for oxygen sweep gas introduction and exhaust gas analysis. Device inlet 610 was connected to a pure oxygen source maintained at atmospheric pressure. Upon exiting device 10 via outlet 620 the sweep gas was passed through a cold moisture trap for dehumidification and then directed through a flow meter and $CO_2$ analyzer. The flowrate was driven by a vacuum pressure station that pulled sweep gas through the entire circuit. Gas pressure drop over device inlet 610 to outlet 620 was monitored using a pressure transducer.

In gathering gas exchange data, water conditions were first measured to ensure that inlet $pCO_2$ and $pO_2$ were within desired range. Acceptance of inlet conditions was followed by recording of water temperature, flowrate, and pressure in the fluid circuit. Also, the sweep gas flowrate, device pressure drop, motor torque, and exhaust $CO_2$ concentration were recorded. The RPM rate was then changed and the procedure was repeated to obtain a minimum of two random data points for each RPM to ensure repeatability.

$CO_2$ removal, $V_{CO2}$, was calculated for the rates by the following equation:

$$V_{CO2} = Q^{STP} F_{CO2} \qquad (2)$$

where $Q^{STP}$ is the flowrate of sweep gas at standard temperature and pressure and $F_{CO2}$ is the fraction of $CO_2$ in the exhaust of the catheter, as measured per the $CO_2$ analyzer. The exchange rate was then divided by the HFM surface area and normalized to the target $pCO_2$ inlet of 50 mmHg to calculate efficiency ($VCO_2$) and normalize variability associated with small changes in inlet $pCO_2$ concentrations:

$$VCO_2 = V_{CO2} \frac{50}{pCO_2^{INLET} \cdot SA} \qquad (3)$$

Figure 9B:
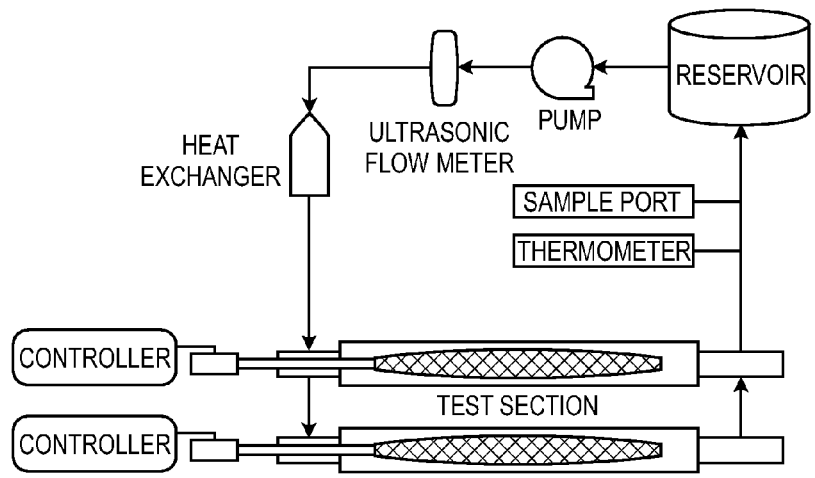
FIG. 9B illustrates an experimental setup for studies of fatigue testing in bovine blood to assess performance of the devices of the present invention.
Figure 9C:
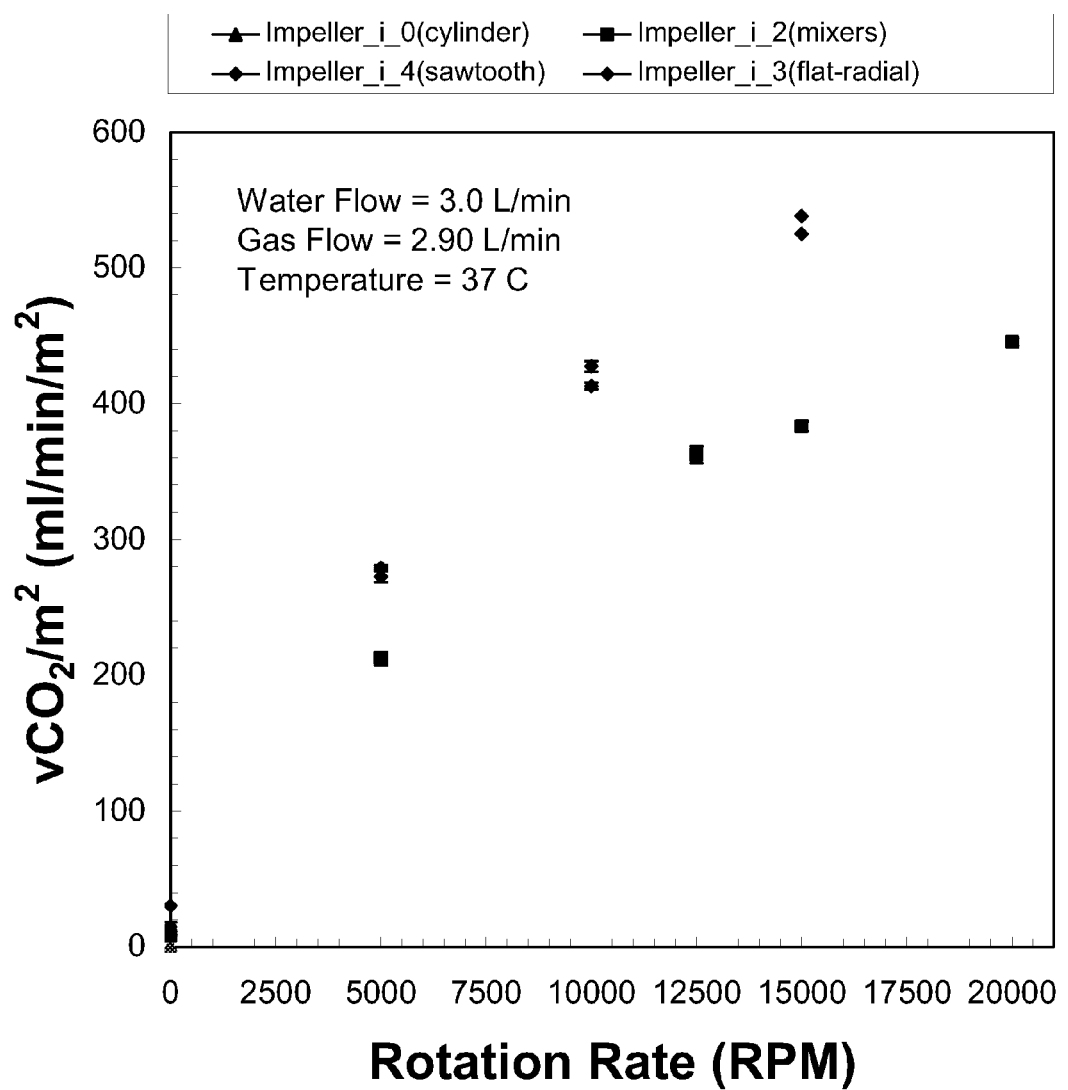
FIG. 9C illustrates a study of carbon dioxide exchange rate per unit area for four impeller geometries of the present invention as a function of impeller rotation rate.
Figure 9D:
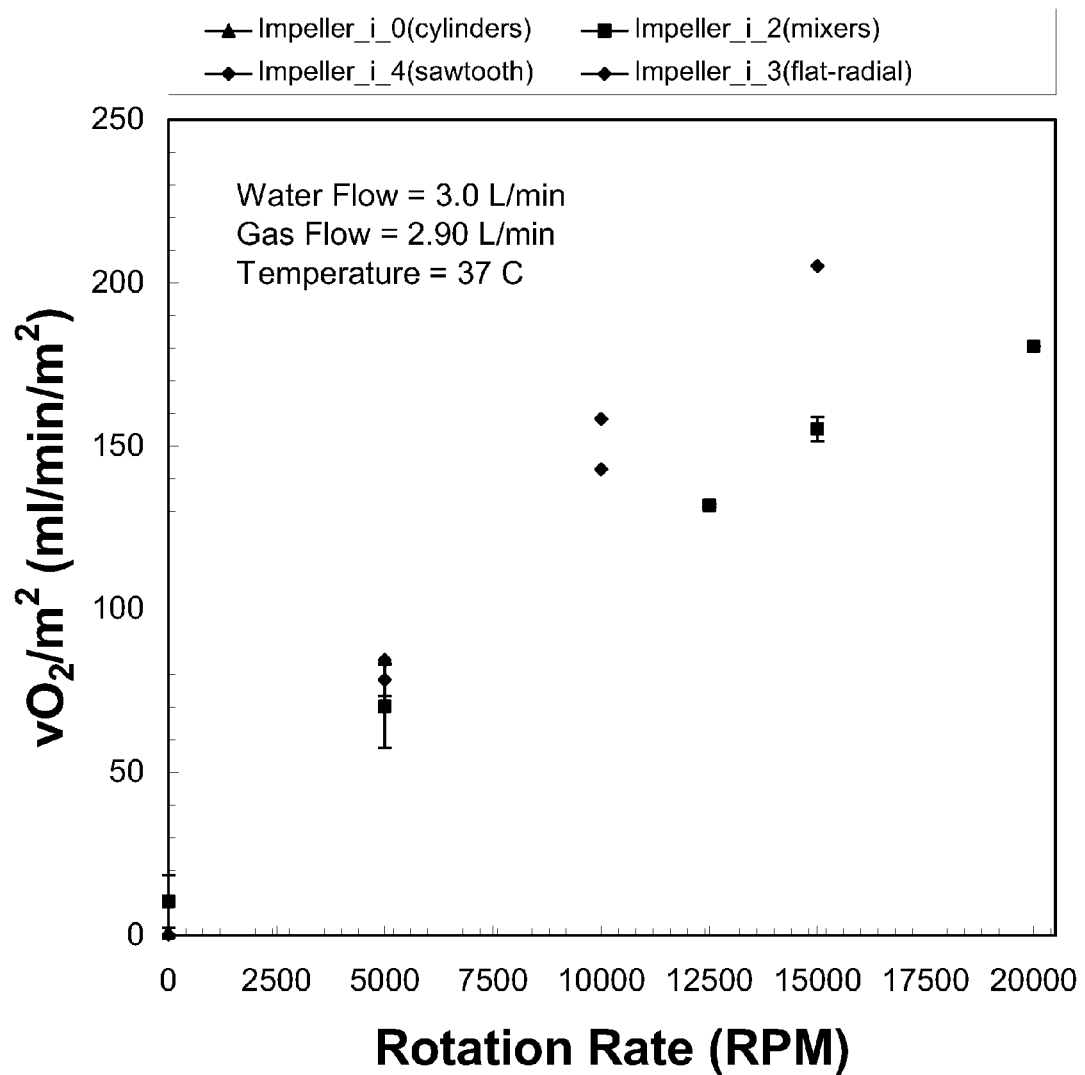
FIG. 9D illustrates a study of oxygen exchange rate per unit area for four impeller geometries of the present invention as a function of impeller rotation rate.

Gas exchange testing evaluated the effect of impeller geometry on $CO_2$ removal efficiency and $O_2$ exchange efficiency. $CO_2$ removal efficiency in deionized water for four different impeller geometries as a function of impeller rotation rate is illustrated in FIG. 9C. $O_2$ exchange efficiency in deionized water for four different impeller geometries as a function of impeller rotation rate is illustrated in FIG. 9D. As described above, in addition to testing in deionized water, $CO_2$ removal efficiency was also measured in a viscous solution. The viscous solution test evaluated the interplay between the impeller transmitting motion to the fluid versus the bundle impeding fluid velocity. A higher viscosity solution, such as blood, transmits fluid motion better thus increasing relative velocity to fiber, whereas the bundle region impedes fluid motion and decreases relative velocity. A 0.4% w/w concentration of carboxymethylcellulose (CMC) sodium salt (#C5678-500G, Sigma-Aldrich Inc.) and DI water was interchanged with homogenous DI water to test prototypes in both solutions. The viscosity of the CMC solution was measured at 37° C. during each test using a capillary viscometer (#150, Cannon Instrument Co) to ensure that the viscosity remained in a range of 2.5-2.7 cP. CMC was used as the solution thickener because a minute concentration could be added to water without altering the gas solubility properties.

Maximum gas exchange in the studies occurred at the peak rotational rate of 20,000 RPM. FIGS. 9E(1) through 9E(9) display prototype characterization plots of $VCO_2$ versus RPM in both testing solutions for the nine impeller unit geometries testes. Maximum $CO_2$ removal efficiencies for all geometries are listed in Table 2. The 4-flat, RAX, sawtooth, and 2-flat geometries performed similarly. Without limitation to any mechanism, it was hypothesized that the centrifugal geometry had a lower efficiency compared to other radial geometries since the ends were enclosed and fluid could not penetrate the vanes as well as open-ended geometries. The cone geometry was the worst performing unit, even when compared to the cylindrical control. Without limitation to any mechanism, it was hypothesized that the tapered end caused the cone unit to have a lower average linear velocity at the surface, which transmitted less momentum to fluid particles, causing the cone geometry to underperform even the control.

TABLE 2

| Impeller | VCO$_2$ (ml CO$_2$/min/m$^2$) |
|---|---|
| control | 307 ± 3 |
| 4-flat | 529 ± 21 |
| RAX | 514 ± 11 |
| sawtooth | 482 ± 6 |
| 2-flat | 482 ± 3 |
| paddle | 457 ± 1 |
| axial | 446 ± 3 |
| centrifugal | 341 ± 2 |
| cone | 264 ± 10 |

The effect of increased viscosity was consistent between geometries. A fluid viscosity in the range of 2.5-2.7 cP decreased gas exchange by approximately 20-30% at 20,000 RPM when compared to water. Without limitation to any mechanism, it is believed that the reduction was a result of increased drag forces on fluid particles as they traversed the HFM bundle. Velocity of a fluid flowing through a porous medium can be theorized according to Darcy's Law which states:

$$\vec{V}o = -\frac{k}{\mu}(\nabla P - \rho\vec{g}) \quad (4)$$

where $\vec{V}o$ is the velocity field vector, k is permeability, $\mu$ is viscosity, $\nabla P$ is the pressure gradient, $\rho$ is fluid density, and $\vec{g}$ is the force of gravity. The fluid velocity through the medium is indirectly proportional to the viscosity and fluids with higher viscosities exhibit lower relative velocities to fibers at a given RPM rate, thus inhibiting boundary layer reduction. This effect was observed in comparing results obtained for the two solutions, per the reduction in efficiency.

CO$_2$ exchange in blood was approximately 20-40% greater than in water when compared, for example, to the intravascular gas exchange device described in Federspiel W J, Hewitt T, Hout M S, et al: Recent progress in engineering the Pittsburgh intravenous membrane oxygenator. *Asaio J* 42: M435-442, 1996, referred to as the HATTLER™ Catheter. Oxygen exchange was also significantly greater.

The blood viscosity resembling solution provided a reference for estimating impeller prototype efficiency enhancement in blood by incorporating relevant viscous effects into the system. The expected increase in efficiency as a result of blood CO$_2$ capacity was similar to the magnitude of efficiency reduction caused by viscosity. Therefore, it was hypothesized that CO$_2$ removal efficiencies in vivo would achieve rates similar to those observed in standard DI water.

A common empirical mass transfer correlation for analyzing oxygenator gas exchange was determined from an analogous heat transfer correlation for perpendicular tube bank flow as follows: $Sh = aRe^b Sc^{1/3}$, wherein Sh is the Sherwood number, Re is the Reynolds number, and Sc is the Schmidt number. The coefficients a, b are dependant on fiber bundle geometry and are determined experimentally, however, coefficient b can be loosely approximated as b=0.5. If the velocity term in the Reynolds number is assumed proportional to rotation rate, VCO$_2$ can be compared to $RPM^{1/2}$ to assess mass transfer. FIGS. 9F(1) through 9F(9) show the correlation for the nine impeller geometries tested on the bench. The linear relationship between VCO$_2$ and $RPM^{1/2}$ indicated that the CO$_2$ driving gradient for gas exchange at higher RPM was not reduced, and therefore was not likely an explanation for the observed leveling trend of gas exchange. The trend was not investigated further. However, without limitation to any mechanism, a second hypothesis to explain the plateau was that specific fiber layers or fiber regions within the bundle were not fully utilized in exchanging gas as result of an inefficient fluid mixing mechanism.

Experiments were also performed to test the effectiveness of the heparinized saline purge by first testing devices of the present invention without saline purge. The tests were conducted in a bench blood circuit to identify whether blood infiltration and subsequent accumulation was responsible for the torsional failures witnessed in the initial in vivo studies described above. Mock devices including only the rotational components were first tested, and results warranted further testing with full prototypes. Two devices were tested in the final fatigue study. The first was a device absent saline purge that served as the test control; while the second was a device with saline purge system.

Both devices were placed in parallel ⅞" test sections within the blood circuit. Blood was re-circulated through each test section at a flowrate of 1.5 LPM and maintained at 37° C. Two liters of blood (Heparinized bovine blood, Hemostat Laboratories) were used in the circuit. The blood was characterized at the beginning for ACT and fibrinogen content. A schematic of the test system is shown in FIG. 9B.

Saline was pumped into each of medial manifold 400 and distal manifold 500 at a flowrate of 12 ml/hr using a peristaltic pump. The drive consoles were programmed to record elapsed time and 1¼ amp fuses were installed into each. The fuses automated the system to shutdown upon failure and permitted the fatigue testing to be conducted overnight under no supervision. The prototypes were operated at a constant speed of 10,000 RPM for the test duration. Motor torque requirements and elapsed time were recorded. All equipment used for fatigue testing is described in Table 4.

TABLE 4

| Component | Model | Manufacturer |
|---|---|---|
| Blood | 2 L heparinized bovine blood | Hemostat Laboratories |
| Ultrasonic flow probe | T110 | Transonic Systems Inc. |
| Reservoir bag | AFFINITY Reservoir Bag #321 | Medtronic Inc. |
| Blood pump | BIO-MEDICUS ® biopump BPX-80 | Medtronic Bio-Medicus Inc. |
| Pump console | 540 BIO-CONSOLE ® | Medtronic Bio-Medicus Inc. |
| Pediatric heat exchanger | D1078 | Medtronic Biotronics |
| Thermometer | DIGI-SENSE ® type T thermocouple | Cole-Parmer Instrument Co. |
| Temperature pump | T/Pump TP-406 | Gaymar Industries |
| Peristaltic pump | MASTERFLEX ® C/L 77120-62 | Barnant Company |

Figure 10:
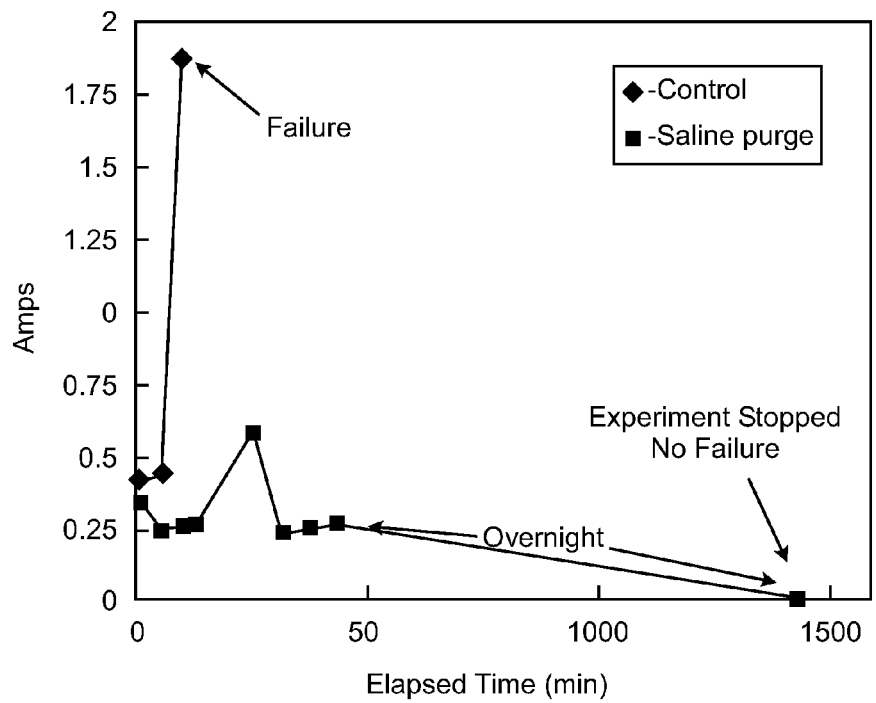
FIG. 10 illustrates a graph of motor current versus elapsed time for a control and for a device of the present invention including saline purge.

Results of preliminary component and full prototype blood fatigue tests showed the saline purge to be an effective means for preventing torsional impeller tubing failures. In the full prototype experiment, device 10 with saline purge was operated for 24 hours and did not show indication of potential failure. The test was discontinued because the operating time far exceeded that necessary to complete an acute bovine study. The device without saline purge, however, failed two hours after the test start. A plot of motor current requirement versus elapsed time is shown in FIG. 10. It is observed that the device with saline purge operated at a constant torque until test completion (motor torque is proportional to motor current). An increase in torque to failure was observed for the device without saline purge as a result of build-up of blood constituents within the annular space between materials/sleeves 408 and 508 and connector sections 122 and 124, respectively.

Blood accumulation was confirmed in the control device (without saline purge) by dissecting the prototypes and examining rotational components. The observed build-up of blood constituents replicated observations of failed devices earlier studied in vivo. In contrast, observation of the device with saline purge revealed seals and material/sleeves 408 and 508 free from blood contact. The saline purge was implemented for subsequent in vivo evaluations.

Testing was transitioned from the bench to an in vivo environment to evaluate device performance in a physiological setting. All in vivo studies performed were acute studies with the objective of obtaining $CO_2$ exchange measurements in a bovine model. The three impellers determined from bench gas exchange characterizations to provide the best $CO_2$ efficiency were the 4-flat, RAX, and sawtooth impeller unit designs. Those three impeller unit designs were used in all further in vivo testing. Gas exchange was measured in two different vena cava positions. The first location was a position spanning the right atrium where longitudinal blood flow in the IVC and a cross-flow into the right atrium were experienced. The second position evaluated the catheter solely in the IVC where only longitudinal flow past the device occurred.

All experiments were performed at a University of Pittsburgh animal facility possessing the proper staff and surgical equipment to provide full animal care. The surgical procedure and testing protocol were authorized by the University of Pittsburgh IACUC. Calves weighing approximately 100-125 kg were used in the experiments. Each animal was fitted with a Swan-Ganz catheter and femoral pressure line following anaesthetization. Heparin infusion was administered into the femoral vein to maintain activated clotting times (ACTs) above 500. Guidewires for device insertion were laid through the jugular vein and femoral vein using a 2-cupped magnet system. The jugular vein was exposed and an incision was made. Upon insertion the device was extended through the jugular vein into the vena cava to situate in either of the two locations described above.

All equipment used in the gas circuit for bench exchange characterization was used. $CO_2$ removal efficiency was calculated in accordance to equations (2) and (3). The purge flowrate was 12 ml/hr of 1:50 heparin to saline solution. The femoral blood $pCO_2$ was maintained in the range of 45-55 mmHg by adjusting ventilator settings.

Testing protocol began when calf femoral $pCO_2$ stabilized within the requested range. The prototype was tested over the full RPM range of 200-20,000 RPM in a randomized fashion. $CO_2$ exhaust concentration, sweep gas flowrate, sweep gas pressure drop, and torque were acquired at rates of 200, 5,000, 10,000, 15,000 and 20,000 RPM. Each data point was obtained at least twice to ensure repeatability. The protocol was initiated in both vena cava locations before a different impeller prototype was inserted. Calve arterial and femoral pressures were monitored and plasma free hemoglobin samples were obtained through the course of testing. Following the experiment, a necropsy was performed to view the vasculature. Prototypes were later dissected on the bench to observe any thrombus formation, failure sites, and seal wear/appearance. A concise outline of the protocol is set forth in Appendix C.

Figure 11:
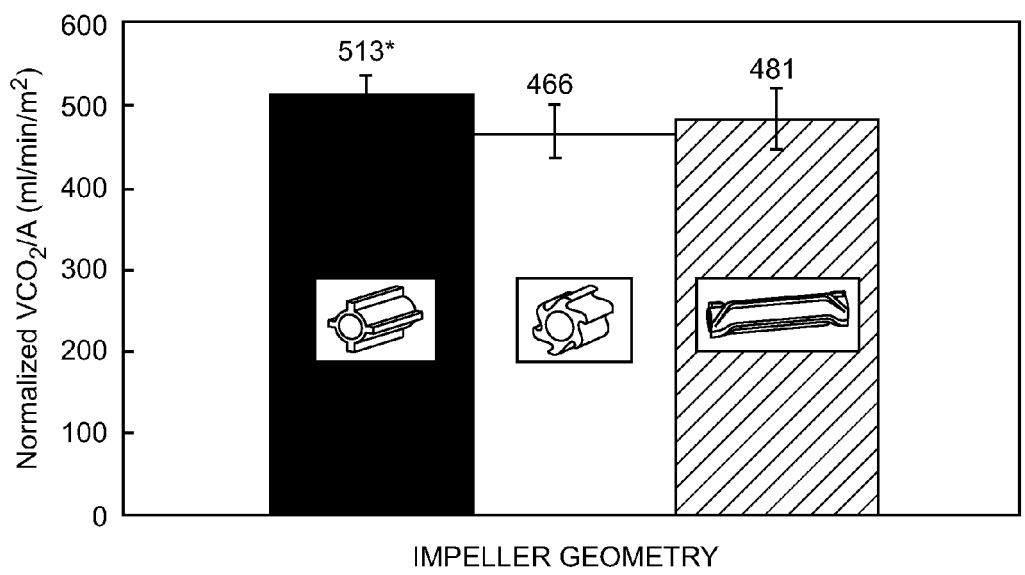
FIG. 11 illustrates a graphical representation of carbon dioxide removal rate per unit area in an animal study for three impeller geometries of the present invention.

Impeller catheter gas exchange data was obtained in four different calves. The results of impeller geometry influence matched the trend identified in bench-testing. FIG. 11 shows the maximum average $CO_2$ removal efficiencies for 4-flat, RAX, and sawtooth impellers. The 4-flat geometry produced the most favorable efficiency level and was found to be significantly higher than the sawtooth geometry. The corresponding in vivo removal rates were: 36 ml $CO_2$/min for 4-flat, 34 ml $CO_2$/min for RAX, and 33 ml $CO_2$/min for sawtooth.

Figure 12:
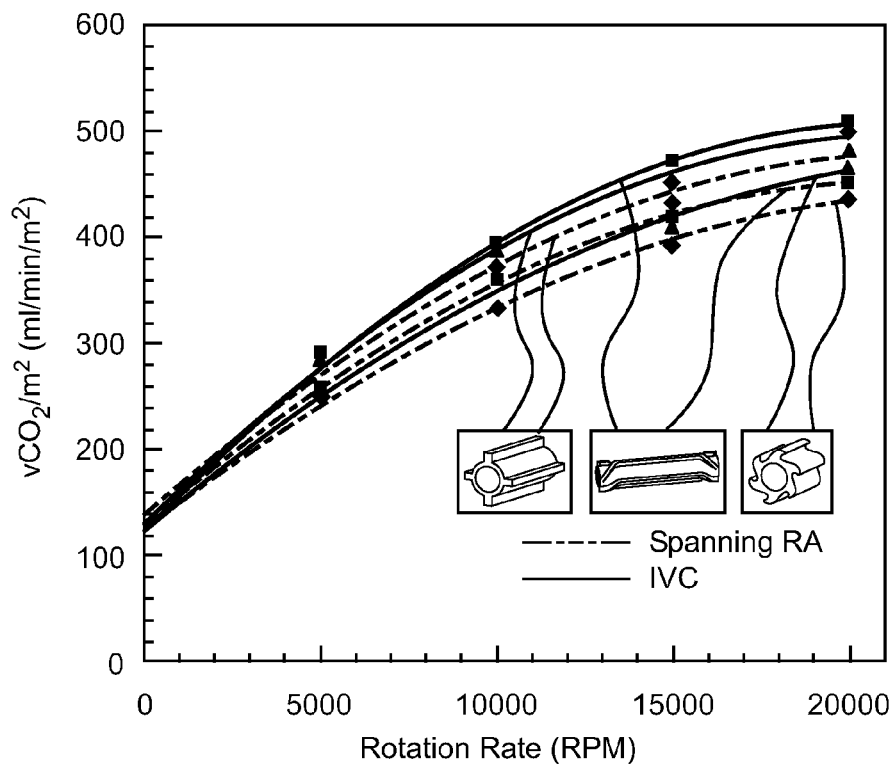
FIG. 12 illustrates carbon dioxide removal rate per unit area in an animal study for three impeller geometries of the present invention as a function of impeller rotation rate. For each device results are shown for two different positions within the animal vena cava, one of which has the device spanning the right atrium

A typical plot of efficiency versus RPM is displayed in FIG. 12. Gas exchange increased as a function of rotational rate. The slope of the curve, however, began to trend towards zero near 20,000 RPM indicating a maximum efficiency plateau. An inspection of all data did not show device location spanning the right atrium to be more beneficial in comparison to the IVC. Any conclusion from the above observations may be limited by the necessity to configure the prototype in vena cava positions avoiding severe tortuousness which may have exposed the catheter to the right atrium mixing in both intended locations.

Maximum removal efficiencies in blood were very similar to bench gas exchange results obtained using normal DI water. Without limitation to any mechanism, it was hypothesized that an increase in $CO_2$ removal over DI water was not observed in blood because the ability of blood to carry a higher $CO_2$ content was offset by the increased bundle drag forces and consequent reduction in relative fluid velocity resulting from a higher fluid viscosity. Bench-testing of devices 10 in standard DI water should thus provide an accurate prediction of maximum $CO_2$ exchange. Oxygen exchange in blood are observed to be 2-3 time greater than that observed in deionized water.

Figure 13:
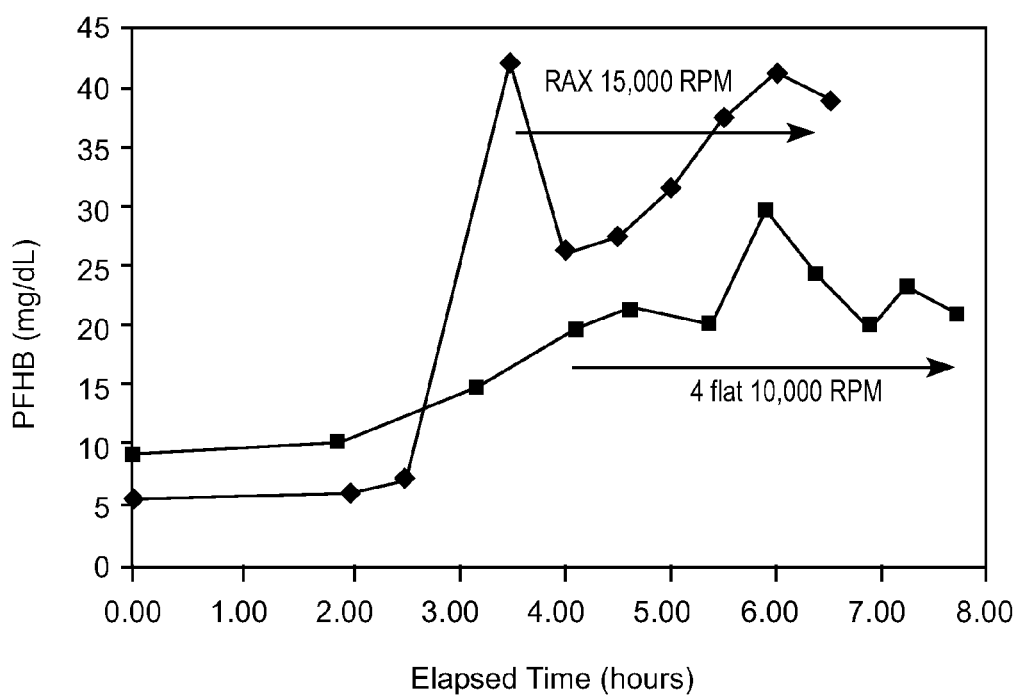
FIG. 13 illustrates blood plasma free hemoglobin (PFHB) levels as a function of time in two animal studies for two impeller geometries of the present invention.
Figure 17:
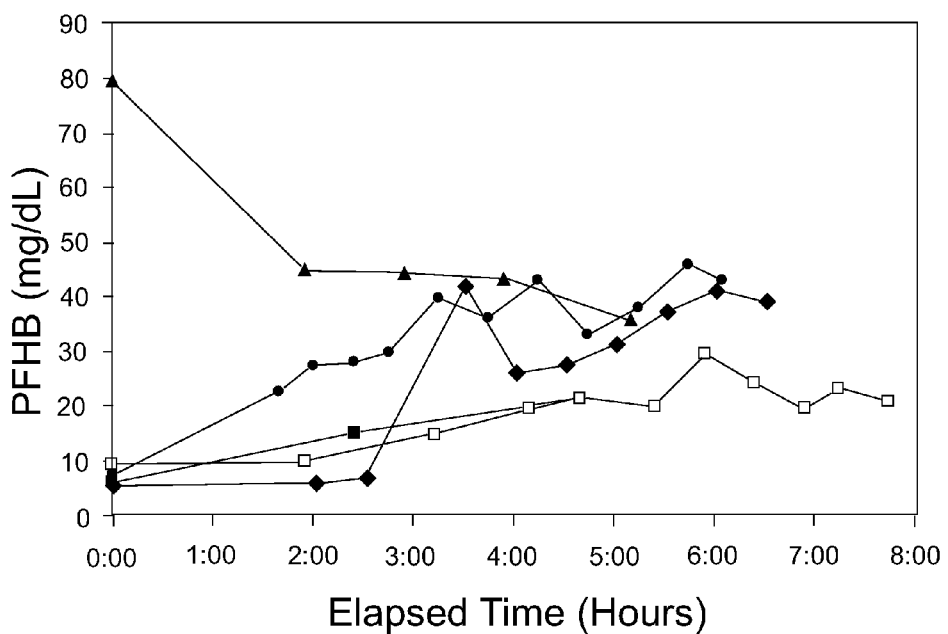
FIG. 17 illustrates a study of hemolysis generation in several animal implant studies.

Once again, plasma free hemoglobin (PFHB) samples were measured during testing. At least three devices 10 were inserted per calf. Data from two studies in which a specific impeller was evaluated over three hours is shown in FIG. 13. FIG. 17 illustrates a plot of PFHB versus elapsed time for all experiments. The prototypes appeared to generate consistent levels between 20-40 mg PFHB/dL that trend towards a constant or decreasing rate. Although devices 10 and impeller units 100 were not optimized, undesirable levels of hemolysis were not observed during testing.

The non-optimized impeller catheters of the present invention enhanced in vivo $CO_2$ removal efficiency by 70% over, for example, the HATTLER Catheter and confirmed the effectiveness of rotation. The device was capable of operating in tortuous vasculature while protecting the vena cava wall. The tradeoff in HFM surface area to reduce size however, reduced overall $CO_2$ removal rates. Removal rate was ultimately higher in the HATTLER Catheter because of its 2½ fold greater surface area. Table 4 sets forth an overview of catheter performance for the HATTLER catheter and impeller device 10 of the present invention.

TABLE 4

| Catheter | Surface Area ($m^2$) | In vitro Efficiency (ml $CO_2$/min/$m^2$) | In vivo Efficiency (ml $CO_2$/min/$m^2$) | $CO_2$ Removal Rate (ml $CO_2$/min) |
|---|---|---|---|---|
| HATTLER Catheter | 0.17 | 230 | 300 | 51 |
| Impeller | 0.07 | 529 | 513 | 36 |

In the devices, systems and methods of the present invention, $CO_2$ removal increases in proportion to $CO_2$ tension in blood. Respiratory catheter data from acute animal implants (calves and sheep) in which ventilatory challenges were done to vary the venous $PCO_2$ were regressed. The resulting correlation ($r^2$=0.993) from 25 mmHg to 70 mmHg: $\dot{V}_{CO2}/\dot{V}_{CO2}^{50\ mmHg}=1.32(10^{-4})P_{CO2}^2+8.05(10^{-3})P_{CO2}+0.26$ predicts an increase in the $CO_2$ removal rate of 50% from normocapnia (45-50 mmHg) to permissive hypercapnia (~70 mmHg). Thus, removal rate of $CO_2$ can be increased approximately 50% by operation under conditions of permissive hypercapnia.

Immobilizing carbonic anhydrase enzyme onto the hollow fiber membranes of the devices of the present invention as described in U.S. patent application Ser. No. 11/811,265 and PCT International Patent Application No. PCT/US2007/013563 (PCT Publication No. WO 2007/146162), the disclosure of which are incorporated herein by reference, further increases $CO_2$ efficiency. Preliminary data using current (baseline) immobilization of CA on hollow fibers (activity~0.002 U/cm$^2$) indicated a 25% increase in the $CO_2$ removal rate in blood. Improved immobilization methods have increased CA activity by 250%.

Agitation mechanisms such as rotating impellers increase gas exchange by reducing the size of diffusional boundary layers that dictate gas exchange. Immobilized CA increases $CO_2$ exchange by creating facilitated diffusion of $CO_2$ as bicarbonate ion, resulting in a larger effective diffusion coefficient for $CO_2$. As such, the effects would be additive. However, such effects may be more than additive because as the boundary layer is reduced, so is the amount of native CA (i.e. in red cells) within the boundary layer, with which immobilized CA competes. Preliminary studies indicate that without native CA (i.e. using bicarbonate buffer as the test fluid), the same immobilized CA fibers increased the $CO_2$ removal rate by 75%.

As set forth above, carbonic anhydrase catalyzes blood bicarbonate into carbon dioxide and increases the fundamental $CO_2$ exchange driving gradient. In that regard, carbon dioxide is present in blood in three primary forms: $CO_2$ (dissolved), bicarbonate ($HCO_3^-$), or carbamate. As known in the chemical arts, $CO_2$ is interconvertible among these forms and the various forms can be in equilibrium with each other as described by a $CO_2$ dissociation curve. Most of the $CO_2$ in blood, however, exists in the form of $HCO_3^-$ in plasma and in red blood cells. Colton C K. 1976. Fundamentals of gas transport in blood. In: Zapol W M and Qvist J, editor. Artificial lungs for acute respiratory failure. Washington D.C.: Hemisphere Publishing Corporation. p 3-43. In that regard, approximately 94% of plasma $CO_2$ and 82% of red blood cell $CO_2$ is in the form of $HCO_3^-$. The two species are interconvertible via the reaction:

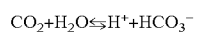

$$CO_2+H_2O \leftrightharpoons H^+ + HCO_3^-$$

The $CO_2$ generates via metabolic pathways in tissue and diffuses into red blood cells (RBCs), where it is hydrated into $HCO_3^-$ and hydrogen ions ($H^+$) by intracellular carbonic anhydrase (CA). The hydrogen ions formed are bound to hemoglobin while $HCO_3^-$ is diffused into plasma. However, very little $CO_2$ is hydrated in plasma because of a lack of CA in plasma. In lungs, the reaction is reversed. $HCO_3^-$ is converted into $CO_2$ via CA in red blood cells, and then exhaled. Some CA exists in lung tissue.

Figure 14A:
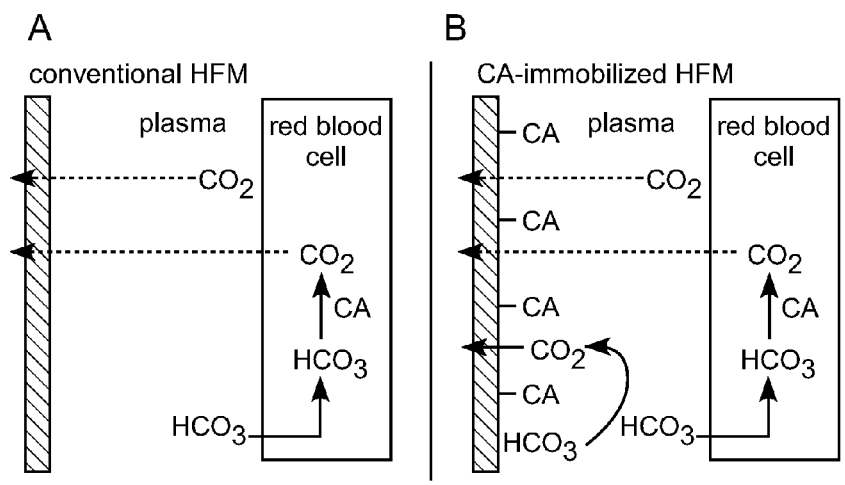
FIG. 14A illustrates a comparison of the operation of a standard hollow fiber membrane with a membrane of the present invention in which diffusion is facilitated by carbonic anhydrase immobilized on or in the vicinity of the membrane surface in contact with the blood plasma (which occurs because the immobilized enzyme generates diffusion of bicarbonate ion (an alternative form of $CO_2$), which is a substrate of the enzyme, towards the membrane, at which the bicarbonate ion is converted to $CO_2$, which then diffuses into and across the membrane).

With reference to FIG. 14A, the immobilized enzyme facilitates diffusion of the specific $CO_2$ through the membrane by generating diffusion of $HCO_3$ to the surface of the membrane. At the membrane surface the enzyme converts $HCO_3$ to $CO_2$.

Figure 14B:
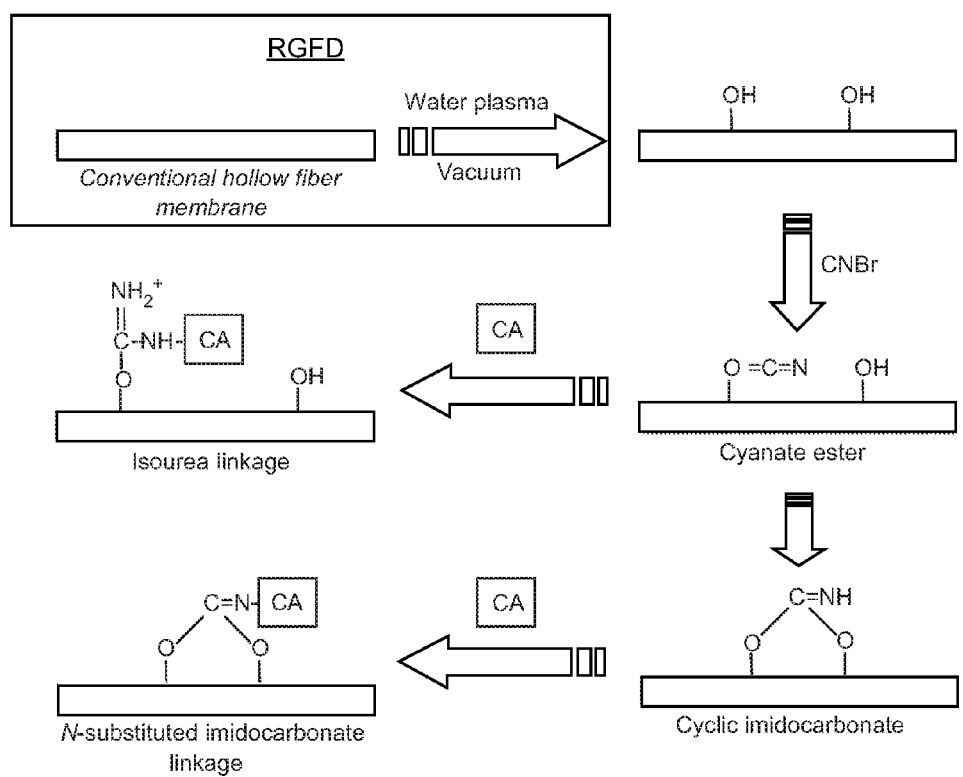
FIG. 14B illustrates a schematic representation of an RFGD process for immobilization of carbonic anhydrase on a polymeric material.

CA maintains substantial activity upon immobilization (for example, via covalent bonding to a polymeric material). As set forth in FIG. 14B, radio frequency glow discharge (RFGD) and cyanogen bromide (CNBr) activation chemistry can, for example, be used to immobilize CA on (or in the vicinity of) at least a first or outer surface of the fibers of the HFM via covalent bonding as described in U.S. patent application Ser. No. 11/811,265 and PCT International Patent Application No. PCT/US2007/013563 (PCT Publication No. WO 2007/146162).

The activity of immobilized CA on fiber surfaces can, for example, be increased by incorporating a base layer of poly (L-lysine) (PLL) or dendritic polyamidoamine (PAMAM) on hollow fibers prior to immobilizing CA. Successive "layers" of CA can be added onto the first immobilized layer using glutaraldehyde-linked "layering".

EXPERIMENTAL SECTION

A. Tortuous Loop Component Tests. The following provides a brief discussion of tests and results of component function in a tortuous environment. The tests were also beneficial for determining a length of impeller units suitable to retain flexibility. Three impeller shaft tubings were tested in the tortuous loop setup to evaluate torque requirements, fatigue, and impeller length. The sample group is set forth in Table A-1 below.

The testing device was placed in a loop and water was circulated to provide a fluid environment. The test device was a "skeleton" impeller prototype in which tubing samples could be easily substituted. Testing was performed without a HFM bundle except in one instance to evaluate the effect of the bundle decreasing bending radii. Torque was calculated by measuring the current into the drive system and converting by means of the motor torque constant.

TABLE 0-1

Selected tubings for tortuous testing.

| Manufacturer | Part # | Material | Mesh | Sealant Topcoat |
|---|---|---|---|---|
| (A) New England Wire Technologies | NEC00029 | Clear PEBAX 6333 | 40 AWG 304 stainless steel | NA |
| (B) New England Wire Technologies | N98-TOL-664 | Blue PEBAX | 44 AWG 304 stainless braid | NA |
| (C) S. S. White Bi-directional hollow shaft coil | 067N133C | Stainless Steel | NA | In-house polyurethane |

The final results of all testing indicated that candidate B of Table A-1 was a preferred candidate. In that regard, the tubing could withstand rotation at 20,000 RPM in the tortuous loop and also provided the largest inner diameter to reduce resistance against sweep gas flow.

Figure 15A:
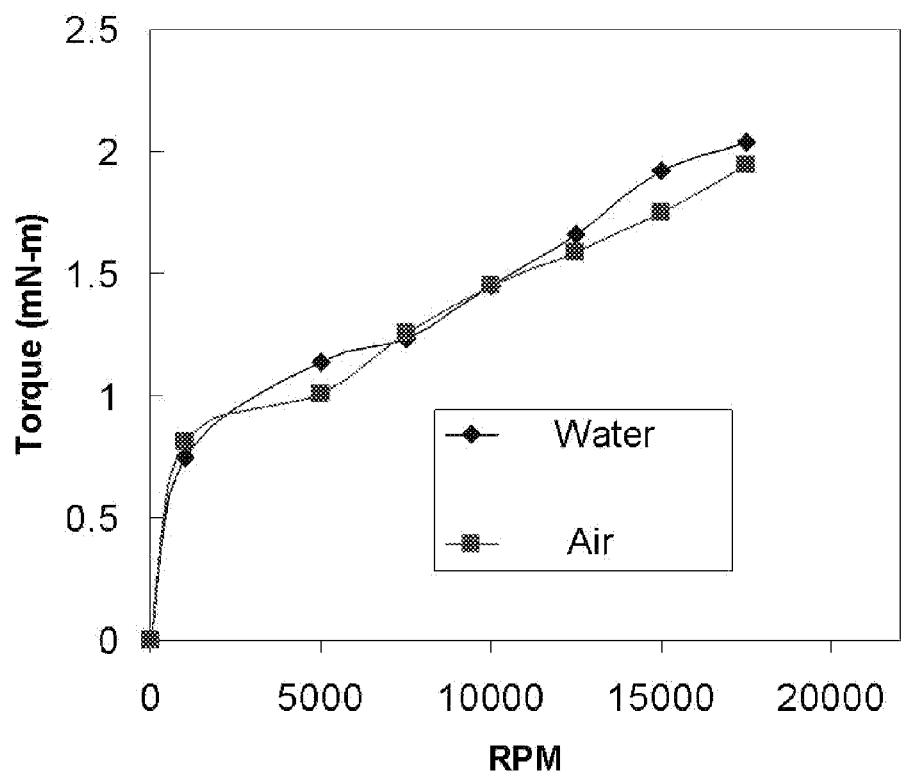
FIG. 15A illustrates a study of the effect of fluid viscosity on required motor torque.

A.1. Effect of Fluid Viscosity on Torque. Testing was performed in a straight test section to evaluate whether fluid viscosity would have a noticeable effect on torque transmission. This was done to ensure that testing in water was suitable and that an increase in viscosity to that of blood would not add excessive torque to the motor or tubing that should be considered. The test was performed using tubing sample A in both water and air. FIG. 15A shows that fluid viscosity had a negligible effect in our applicable ranges.

Figure 15B:
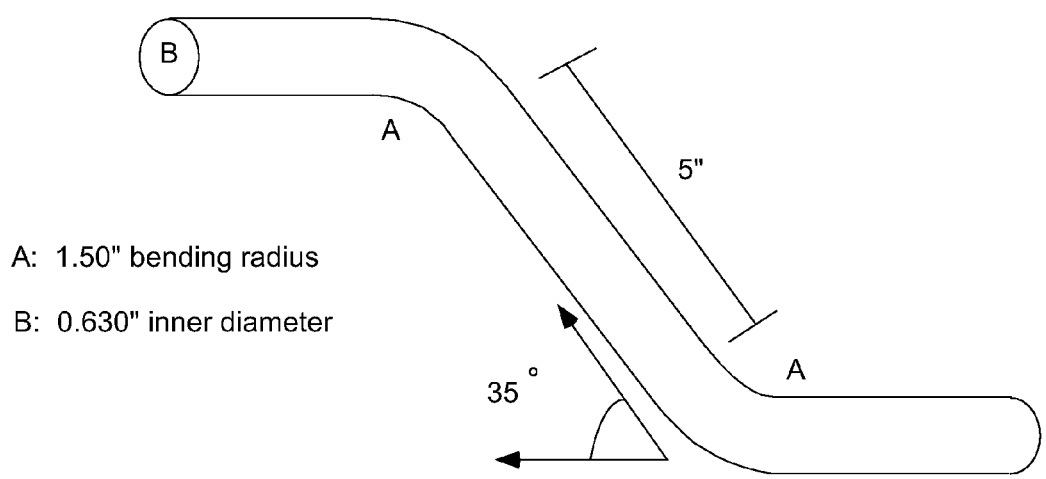
FIG. 15B illustrates a tortuous test section used in studies of the present invention.

A.2. Impeller Unit Length. All impeller units were fabricated from rigid materials and thus constrained tubing flexibility. Fixing the units to the impeller tubing required both a unit length and spacing to be determined. The spacing between units was arbitrarily set at 0.5" (inches). Sample C was tested in the loop with two impeller configurations consisting of either 1" impeller units or 0.5" impeller units. The test was conducted at 20,000 RPM and 1" units were concluded to provide inadequate flexibility. The longer units constrained the tubing to greater bending stresses in between units. A portion of the testing configuration is represented in FIG. 15B.

Figure 15C:
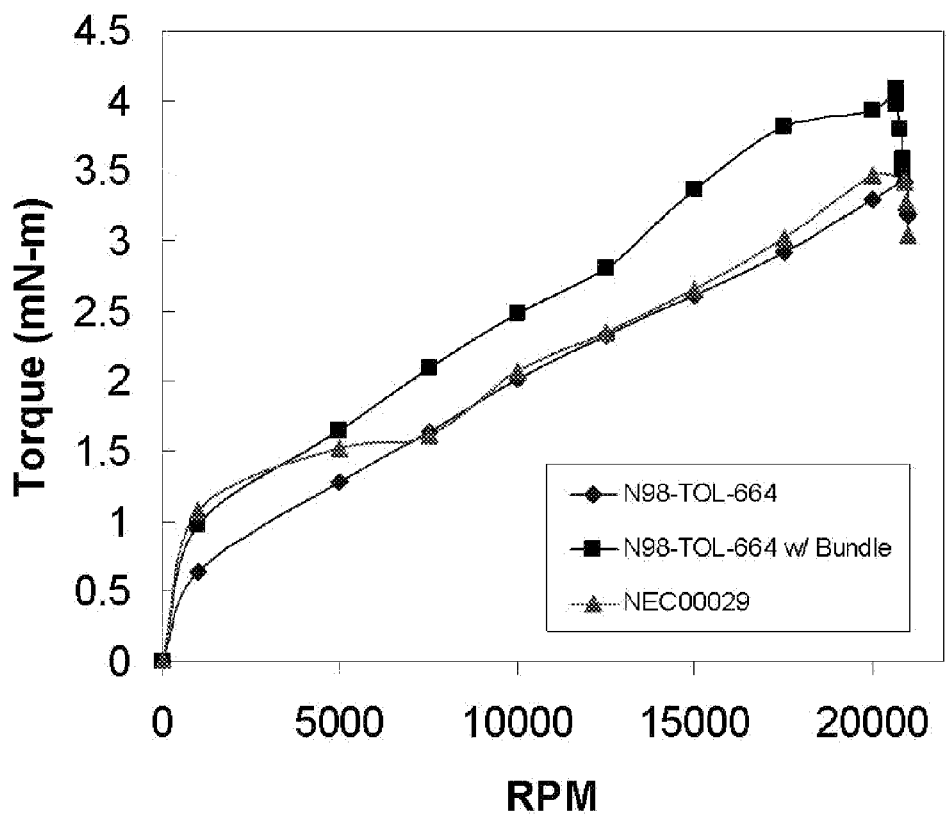
FIG. 15C illustrates a study of measured torque levels of tubing samples in tortuous configurations.

A.3. Fatigue and Torque Requirement. Test devices were placed in the tortuous configuration represented in FIG. 15B and operated at 20,000 RPM for fatigue life. Elapsed time and motor torque were monitored. A HFM bundle was also added to the N98-TOL-664 tubing test device to observe the effects on torque as bending radii decreased. Torque versus RPM results for tubing samples A and B are shown in FIG. 15C. Both samples ran for over 6 hours without failure and were deemed usable in the prototype. The samples performed similarly in regards to torque requirement in the loop and the HFM bundle was observed to increase motor torque by an insignificant 0.5-1 mN-m. The recommended continuous torque application for the brushless servomotor was 13.5 mN-m and thus torque required in the "worst-case" scenario tortuous loop was still 3 times lower indicating motor-prototype compatibility.

B. Impeller Catheter Design Calculations. The blood shear stress calculations indicated a plausible cause for build-up observed in the external VESPEL sleeves during initial in vivo testing. A flushing fluid (saline) purge calculation was used to meet a design requirement of 200 mmHg gauge pressure at the seal interface.

Figure 16A:
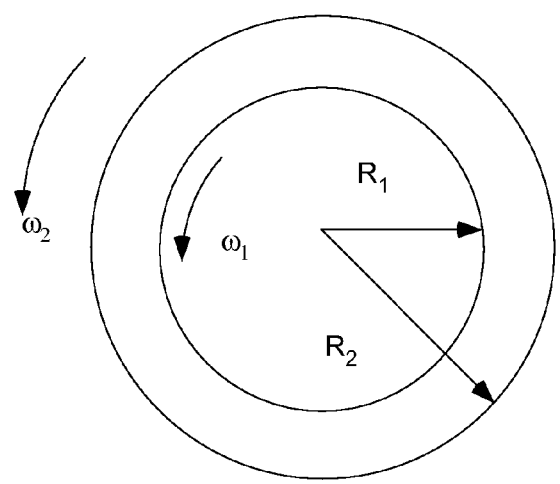
FIG. 16A illustrates a schematic representation of concentric rotating cylinders.

B.1. Blood Shear Stress Calculation. Shear stress calculation for fully-developed, steady flow between concentric cylinders with outer cylinder fixed ($\omega_2=0$) (as graphically represented in FIG. 16A):
Laminar Flow (Re<1700) between Rotating Cylinders when $\omega_2=0$:

$Re = \omega_1 R_1 \delta / \nu$ where $\delta = R_2 - R_1$

Shear stress $\tau_1$, on the inner cylinder is:

$$\tau_{r\theta} = -\left[\mu r \frac{d}{dr}\left(\frac{V_\theta}{r}\right)\right]_{r=R_1} \quad \text{where } V_\theta = \frac{R_1^2 \omega_1}{R_2^2 - R_1^2}\left(\frac{R_2^2}{r} - r\right)$$

$$\therefore \tau_{r\theta} = \frac{2\mu R_2^2 \omega_1}{R_2^2 - R_1^2}$$

Calculation for impeller rotation at 20,000 RPM:

$$\omega_1 = 20,000 \cdot \frac{2\pi \text{ rad}}{60 \text{ s}} = 2094 \frac{\text{rad}}{\text{s}}$$

$\mu_{blood} = 0.033$ P $\nu_{blood} = 0.031$ cm$^2$/s $R_1 = 0.142$ cm $R_2 = 0.144$ cm At 20,000 RPM, Re=19.2<1700 ∴ flow is laminar $$\tau_{r\theta} = 5010 \frac{\text{dyne}}{\text{cm}^2}$$

Figure 16B:
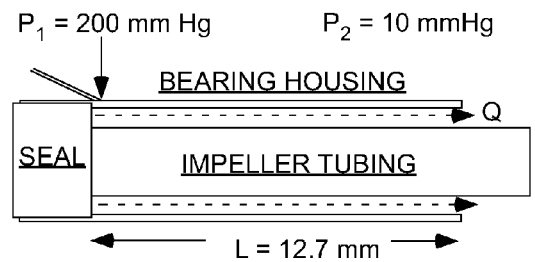
FIG. 16B illustrates schematically a side view an embodiment of an impeller catheter external sleeve.
Figure 16C:
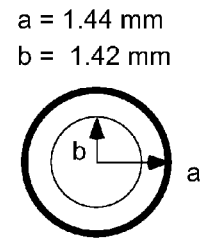
FIG. 16C illustrates schematically a front view an embodiment of an impeller catheter external sleeve.

B.2. Saline Purge Flow Rate Calculation. Flow through an annulus (see FIG. 16B) is calculated according to:

$$Q = \frac{\pi}{8\mu}\left(-\frac{dP}{dx}\right)\left[a^4 - b^4 - \frac{(a^2 - b^2)^2}{\ln(a/b)}\right]$$

Assume linear pressure gradient:

$$-\frac{dP}{dx} = \frac{P_2 - P_1}{L}$$

$P_1 = 26,664$ Pa $P_2 = 1,333$ Pa $\mu = 0.001$ Pa-s $L = 0.0127$ m $a = 0.001435$ m $b = 0.001422$ m $$Q = 3.28 \times 10^{-9} \frac{m^3}{s} = 12 \frac{ml}{hr}$$

C. Impeller Prorotype In Vivo Protocol.

C1. Impeller Catheter Acute In vivo Test Protocol. In several studies the impeller catheter of the present invention was evaluated in a calf model for gas exchange and hemodynamics at various rotation rates. The results were compared with gas exchange results to in vitro water data.

Devices: 1. Impeller: Vadnais coil tubing with PEBAX heat-shrink/4-flat impeller units/saline purge
2. Impeller: Vadnais coil tubing with PEBAX heat-shrink/RAX impeller units/saline purge
3. Impeller: Vadnais coil tubing with PEBAX heat-shrink/sawtooth impeller units/saline purge Protocol:
Pre-Test Preparation (Previous Day):
1) Calibrate all equipment (Gas Flowmeter, Pressure Transducer)
2) Setup equipment and make albumin soaking solution and heparinized saline (0.02 v/v)
Day of Test:
1) Calibrate $CO_2$ analyzer.
2) Soak device in albumin/heparin solution. (50 cc bovine albumin, 10 cc heparin, and saline)
3) Fill moisture trap container with ice.
4) Take baseline blood samples.
5) Insert all necessary pressure lines and take baseline measurements (CO, pressures):
Left femoral vein
Carotid artery
Swan-Ganz—CVP and CO
6) Measure diameter of right external jugular vein once exposed.
7) Measure initial hematocrit and CO, then begin volume loading with lactated ringers at 15 ml/kg. After volume loading, measure hematocrit and CO again.
8) The magnetic guide system will be inserted via the right femoral vein and right external jugular vein, using Fluoroscopy.
9) Pull wires back and attach distal tip of catheter to femoral guide wire.
10) Allow 2 minutes for saline flush of device to initiate.
11) Administer a heparin bolus through the left femoral line.
12) Insert the catheter into the right jugular with animal positioned on its side.
13) Pull catheter through the jugular vein and position spanning the RA. Verify with Fluoroscopy.
14) Set the gas flow to maximum allowed and begin rotating at 5000 RPM. A post-insertion CO and several gas exchange values should be acquired during the equilibrium phase.
15) When exchange stabilizes, rotation rate protocol will begin.
16) Test the following rotation rates in a random order: 5000, 10000, 15000, 20000 RPM, repeating each point twice. Record % $CO_2$, rotation rate, current, gas flow rate, and gas pressure drop.
17) Reduce the rotation rate and record 200 RPM exchange rate. Obtain a CO at 200 RPM.
18) When finished with all rotation rates, move the device into the IVC.
19) Allow ~15 minute stabilization period with rotation at 5000 RPM. Take another CO.
20) Repeat steps 18-19 in this new location.
21) Remove device and place additional impeller devices. Repeat steps 13-21.
22) Keep the device in the second location for necropsy.
23) Pictures and anatomic measurements will be taken at necropsy.
24) Perform gross examination of organs (lung especially) and send out for histology samples if needed.

C.2. In Vivo Hemolysis Studies. FIG. 17 illustrates measured PFHB during all in vivo testing of the impeller prototype. Each line represents a separate calve experiment. PFHB ranged between 20-40 mg/dL for each animal during prototype testing.

The foregoing description and accompanying drawings set forth the preferred embodiments of the invention at the present time. Various modifications, additions and alternative designs will, of course, become apparent to those skilled in the art in light of the foregoing teachings without departing from the scope of the invention. The scope of the invention is indicated by the following claims rather than by the foregoing description. All changes and variations that fall within the meaning and range of equivalency of the claims are to be embraced within their scope.

What is claimed is:

1. A system for intracorporeal gas exchange comprising:
a flexible, rotatable shaft;
a plurality of axially spaced agitation mechanisms positioned on the rotatable shaft, such that the rotatable shaft can flex between the axially spaced agitation mechanisms;
a medial manifold;
a distal manifold,
a plurality of hollow gas permeable fibers adapted to permit diffusion of a gas between an intracorporeal fluid and an interior of the hollow fibers, the plurality of hollow fibers being positioned radially outward from the agitation mechanisms, a first end of each of the plurality of hollow fibers being in fluid connection with the medial manifold, a second end of each of the plurality of hollow fibers being in fluid connection with the distal manifold;
a first fluid path for flow of an inlet gas into the medial manifold to flow into the first ends of the hollow fibers and a second fluid path in fluid connection with the distal manifold into which an outlet gas exiting the second ends of the hollow fibers can flow to exit the system, wherein at least a first portion of the second fluid path is within the flexible, rotatable shaft;
an extracorporeal proximal manifold comprising an inlet in fluid connection with the first fluid path and an outlet in fluid connection with the second fluid path; and
a drive shaft and a drive system to impart rotation to the drive shaft, the drive shaft passing through the extracorporeal proximal manifold and through a second portion of the second fluid path to be in operative connection with the rotatable shaft.

2. The system of claim 1 further comprising a support member positioned radially outward from the agitation mechanisms, the plurality of hollow fibers being positioned radially outward of and adjacent the support member.

3. The system of claim 2 wherein the support member comprises a helical coil of stainless steel.

4. The system of claim 1 wherein each of the plurality of agitation mechanisms comprises at least one radially outward extending vane.

5. The system of claim 1 wherein the drive shaft is connected to the rotatable shaft by a connector comprising a conduit in fluid connection with the first portion of the second fluid path and with the second portion of the second fluid path.

6. The system of claim 1 wherein the drive shaft is in operative connection with the drive system via the extracorporeal proximal manifold.

7. The system of claim 1 further comprising a vacuum in fluid connection with the outlet of the extracorporeal proximal manifold.

8. The system of claim 1 further comprising a seal and a purge system via which a flushing fluid is introduced under pressure over a blood-side face of the seal and caused to flow through a space on a blood side of the seal.

9. The system of claim 8 wherein the space on the blood side of the seal is in fluid connection with an annular space adjacent to the rotatable shaft.

10. The system of claim 1 further comprising a purge system via which a flushing fluid is introduced under pressure, the medial manifold comprising at least a first seal and the distal manifold comprising at least a second seal, the purge system introducing the flushing fluid under pressure over a blood-side face of the at least a first seal and causing the flushing fluid to flow through a space on a blood side of the at least a first seal, the purge system further introducing the flushing fluid under pressure over a blood-side face of the at least a second seal and causing the flushing fluid to flow through a space on a blood side of the at least a second seal.

11. The system of claim 10 wherein the space on the blood side of the at least a first seal is in fluid connection with an annular space adjacent to a first rotating element operatively connected to the rotatable shaft and the space on the blood side of the at least a second seal is in fluid connection with an annular space adjacent to a second rotating element operatively connected to the rotatable shaft.

12. The system of claim 11 wherein the purge system comprises a first conduit to deliver the flushing fluid to the medial manifold and a second conduit to deliver the flushing fluid to the distal manifold.

13. The system of claim 10 wherein the distal manifold, hollow fibers and medial manifold are adapted to be inserted intravascularly and have a maximum outer diameter of no more than 33 French.

14. The system of claim 13 wherein the maximum outer diameter is not more than 25 French.

15. The system of claim 10 wherein the system comprises immobilized carbonic anhydrase on or in a vicinity of at least a portion of a first surface of the hollow fibers.

16. The system of claim 10 further comprising immobilized carbonic anhydrase on or in a vicinity of at least a portion of a first surface of the hollow fibers such that the immobilized carbonic anhydrase comes into contact with the intracorporeal fluid, wherein the first surface exhibits carbonic anhydrase activity of at least 20% of a maximum theoretical activity of the first surface of the hollow fibers based on a monolayer surface coverage of carbonic anhydrase in a case that the carbonic anhydrase is immobilized on the first surface of the hollow fibers.

17. The system of claim 1 wherein the drive system and drive shaft are adapted to rotate the rotatable shaft at a rate of at least 10,000 to 20,000 RPM.

* * * * *